United States Patent
Zhu

(10) Patent No.: US 9,522,269 B2
(45) Date of Patent: Dec. 20, 2016

(54) NEEDLE AND LEAD AND METHODS OF USE

(76) Inventor: Hui Zhu, Lutz, FL (US)

(*) Notice: Subject to any disclaimer, the term of this patent is extended or adjusted under 35 U.S.C. 154(b) by 889 days.

(21) Appl. No.: 12/633,408

(22) Filed: Dec. 8, 2009

(65) Prior Publication Data
US 2012/0209283 A1 Aug. 16, 2012

Related U.S. Application Data

(60) Provisional application No. 61/120,810, filed on Dec. 8, 2008, provisional application No. 61/145,959, filed on Jan. 20, 2009, provisional application No. 61/227,069, filed on Jul. 20, 2009.

(51) Int. Cl.
*A61N 1/39* (2006.01)
*A61N 1/05* (2006.01)
*A61B 17/34* (2006.01)

(52) U.S. Cl.
CPC ........... *A61N 1/0553* (2013.01); *A61N 1/0551* (2013.01); *A61B 17/3401* (2013.01)

(58) Field of Classification Search
CPC . A61B 19/201; A61B 17/3401; A61N 1/0551; A61N 1/36035
USPC .................... 606/129; 607/117, 43
See application file for complete search history.

(56) References Cited

U.S. PATENT DOCUMENTS

| | | | |
|---|---|---|---|
| 4,046,151 A * | 9/1977 | Rose | 607/127 |
| 4,190,033 A * | 2/1980 | Foti | 600/555 |
| 4,349,023 A | 9/1982 | Gross | |
| 4,721,506 A | 1/1988 | Teves | |
| 4,808,157 A | 2/1989 | Coombs | |
| 4,920,980 A * | 5/1990 | Jackowski | 607/123 |
| 5,184,620 A * | 2/1993 | Cudahy et al. | 600/382 |
| 5,255,678 A * | 10/1993 | Deslauriers et al. | 600/375 |
| 5,255,691 A | 10/1993 | Otten | |
| 5,263,493 A * | 11/1993 | Avitall | 607/122 |
| 5,492,119 A * | 2/1996 | Abrams | 600/375 |
| 5,766,192 A * | 6/1998 | Zacca | 606/159 |
| 5,810,807 A * | 9/1998 | Ganz et al. | 606/47 |
| 5,824,031 A * | 10/1998 | Cookston et al. | 607/122 |
| 5,848,996 A | 12/1998 | Eldor | |
| 5,871,483 A * | 2/1999 | Jackson et al. | 606/41 |
| 5,876,408 A * | 3/1999 | Alt et al. | 606/129 |
| 5,895,416 A * | 4/1999 | Barreras et al. | 607/62 |
| 5,919,155 A * | 7/1999 | Lattin et al. | 604/20 |
| 5,968,012 A * | 10/1999 | Ren et al. | 604/96.01 |
| 6,066,132 A * | 5/2000 | Chen et al. | 606/28 |
| 6,161,047 A | 12/2000 | King | |

(Continued)

OTHER PUBLICATIONS

Spinal Cord Stimulation—Percutaneous Technique, retrieved from web Nov. 1, 2009 (4 pages) URL: http://algotec-ltd.com/files/public/documents/percutaneous.pdf.

*Primary Examiner* — Richard Louis
(74) *Attorney, Agent, or Firm* — Stephen G Stanton

(57) ABSTRACT

A lead adapted to be steerable during insertion into an animal body includes the following. A structure substantially defining at least one principal planar surface, the structure having a proximate end and a distal end. The structure includes a tip portion on the distal end, and a body portion, with the tip portion being flexible in directions substantially parallel to said at least one principal planar surface. A shape of the tip portion is changeable, and an end of the tip portion traces a path within a plane substantially parallel with the at least one principal planar surface. At least one electrode is connected with said structure.

13 Claims, 22 Drawing Sheets

(56) References Cited

U.S. PATENT DOCUMENTS

| | | |
|---|---|---|
| 6,205,361 B1 * | 3/2001 | Kuzma et al. ............ 607/116 |
| 6,308,103 B1 | 10/2001 | Gielen |
| 6,309,401 B1 | 10/2001 | Redko |
| 6,522,932 B1 * | 2/2003 | Kuzma et al. ............ 607/116 |
| 6,553,264 B2 | 4/2003 | Redko |
| 6,554,809 B2 | 4/2003 | Aves |
| 6,714,822 B2 | 3/2004 | King |
| 6,895,283 B2 | 5/2005 | Erickson |
| 7,079,882 B1 | 7/2006 | Schmidt |
| 7,099,718 B1 | 8/2006 | Thacker |
| 7,351,214 B2 | 4/2008 | Burgermeister |
| 7,359,755 B2 | 4/2008 | Jones |
| 7,376,468 B2 * | 5/2008 | King et al. ............... 607/116 |
| 7,386,350 B2 | 6/2008 | Vilims |
| 7,499,755 B2 | 3/2009 | Cross |
| 8,204,607 B2 * | 6/2012 | Rooney et al. ........... 607/130 |
| 2001/0053885 A1 | 12/2001 | Gielen |
| 2003/0069623 A1 | 4/2003 | Stypulkowski |
| 2004/0186378 A1 * | 9/2004 | Gesswein ................ 600/435 |
| 2004/0193032 A1 * | 9/2004 | Mogul .................... 600/374 |
| 2005/0004440 A1 * | 1/2005 | Vanney ................... 600/374 |
| 2005/0209667 A1 * | 9/2005 | Erickson et al. ......... 607/116 |
| 2006/0206183 A1 | 9/2006 | Pyles |
| 2006/0271087 A1 * | 11/2006 | Von Dyck et al. ........ 606/192 |
| 2007/0027514 A1 * | 2/2007 | Gerber ................... 607/116 |
| 2007/0027515 A1 * | 2/2007 | Gerber ................... 607/116 |
| 2007/0100235 A1 * | 5/2007 | Kennedy, II ............. 600/434 |
| 2007/0168007 A1 * | 7/2007 | Kuzma et al. ............ 607/116 |
| 2007/0191709 A1 | 8/2007 | Swanson |
| 2008/0103575 A1 | 5/2008 | Gerber |
| 2008/0132926 A1 | 6/2008 | Eichmann |
| 2008/0188917 A1 | 8/2008 | Gerber |
| 2009/0264973 A1 | 10/2009 | Boling |

* cited by examiner

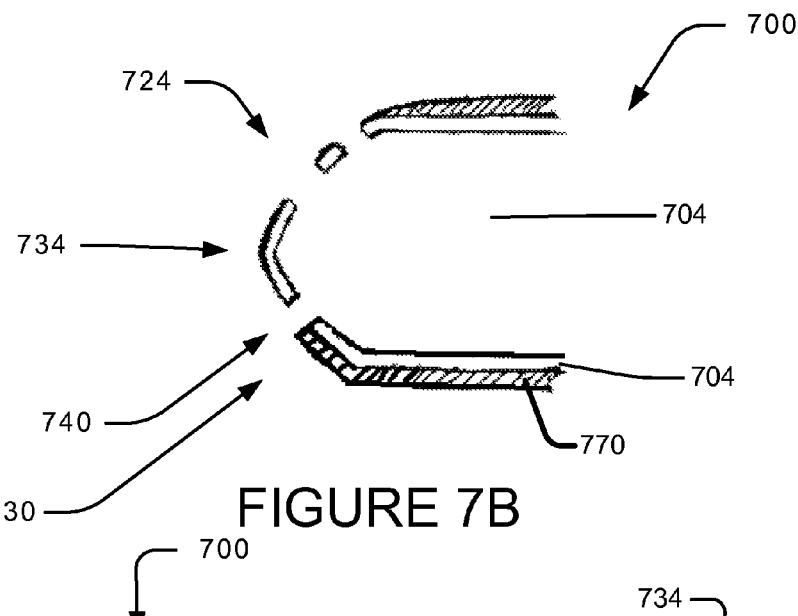
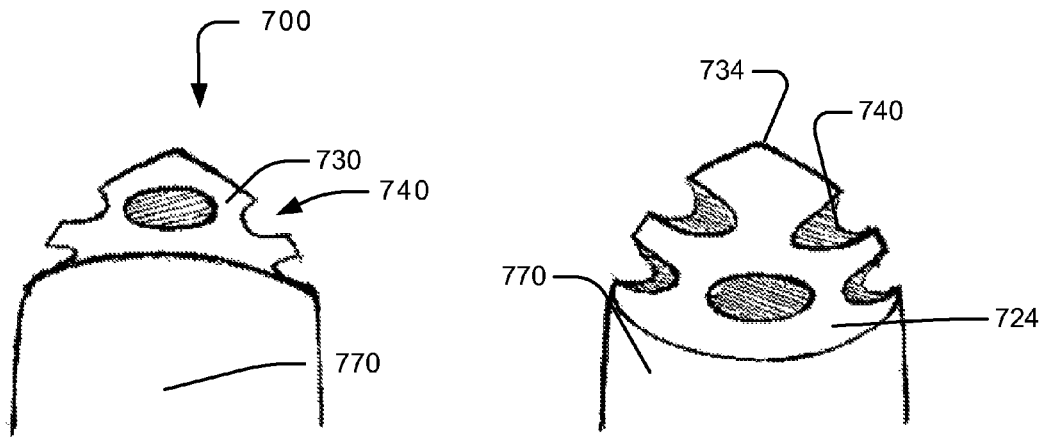
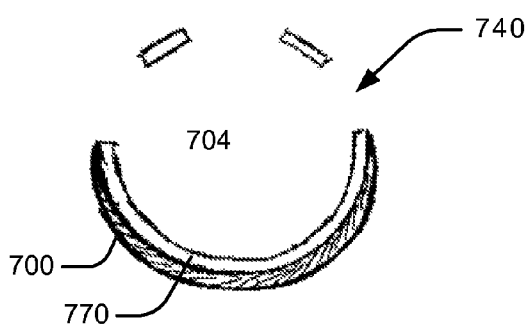
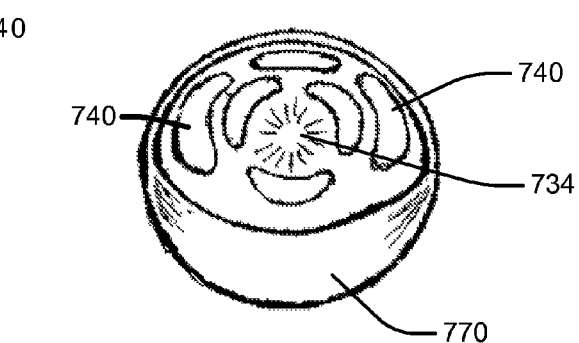
FIGURE 7B
FIGURE 7A
FIGURE 7C
FIGURE 7D
FIGURE 7E

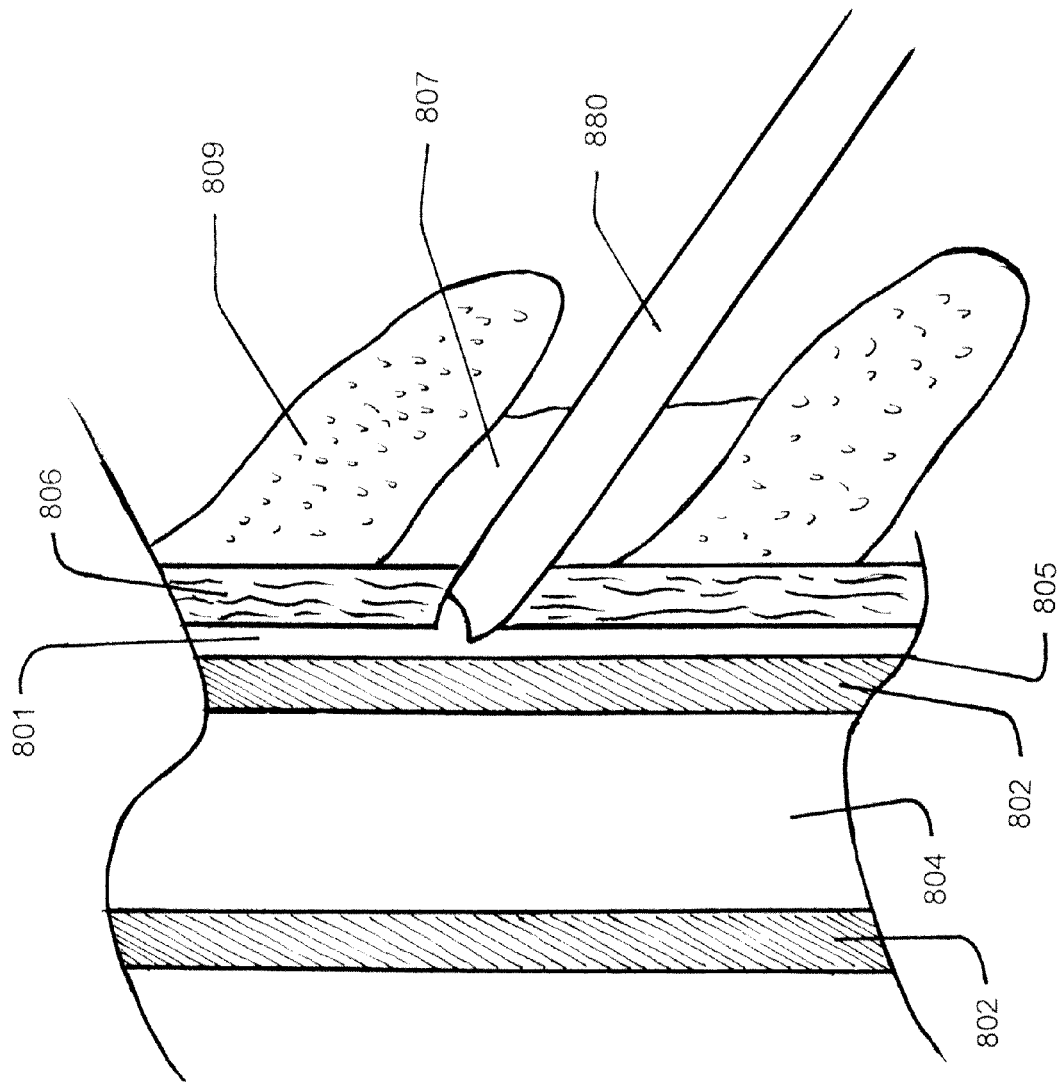

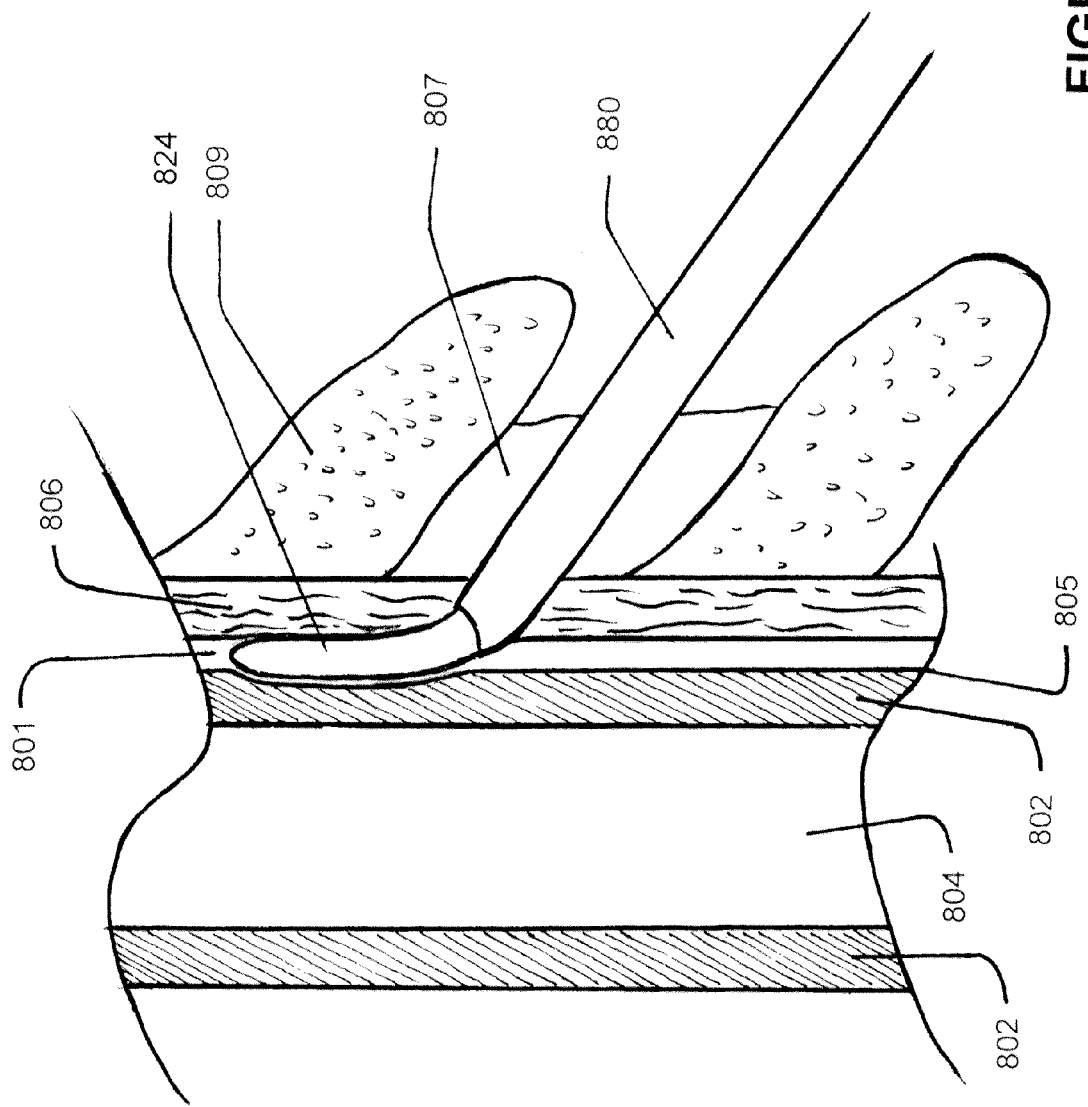

NEEDLE AND LEAD AND METHODS OF USE

CROSS REFERENCE TO RELATED APPLICATIONS

This patent application is a regular patent application (non-provisional) that claims priority at least under 35 U.S.C. 119(e) from the following provisional applications:

| Ser. # | File date | inventor | Title |
| --- | --- | --- | --- |
| 61120810 | 8 Dec. 2008 | Hiu Zhu | Needle assembly and approach for percutaneous introduction of paddle shaped lead to epidural space for neurostimulation |
| 61145959 | 20 Jan. 2009 | Hui Zhu | "Flex-tip" Paddle Lead for Spinal Cord Stimulation and Modification of the "Chisel-tip" Epidural Needle for Percutaneous Insertion of Paddle Lead into Epidural Space |
| 61227069 | 20 Jul. 2009 | Hui Zhu | An alternative Design of "flex-tip" Paddle lead for spinal Cord Stimulation and a modification of the "chisel-tip" needle assembly for safer access of epidural space |

The above applications are herein incorporated by reference in their entirety.

BACKGROUND OF INVENTION

1) Field of the Invention

This invention relates generally to electrical stimulation leads for medical applications and in particular to a method and apparatus for implanting an electrical stimulation lead using a needle and stimulation lead.

2) Description of the Prior Art

Anesthesiologists may non-surgically implant a percutaneous versions of medical leads for spinal cord stimulation (SCS) with Touhy needles. Typically, percutaneous versions of medical leads have been various standard cylindrical styles rather than flattened paddle style leads, which tend to be surgically implanted by surgeons with the associated discomfort, expense and inconvenience of surgical procedures. Paddle-style leads, however, are at least perceived to be more stable in their location after implantation.

There is a need or desire for a paddle-style lead that can be implanted without performing a surgical procedure, such as a laminectomy or laminotomy. Also there are needs for methods and devices for implanting a paddle style lead.

SUMMARY OF THE INVENTION

The following presents a simplified summary in order to provide a basic understanding of various aspects of some example embodiments of the invention. This summary is not an extensive overview of the example embodiments or the invention. It is intended neither to identify key or critical elements of the invention nor to delineate the scope of the invention. Rather, the primary purpose of the summary is to present some example concepts of the example embodiments of the invention in a simplified form as a prelude to the more detailed description that is presented later.

Some example embodiments of the present invention provide a needle, needle assembly, sheath and medical leads and methods of use and combinations thereof.

An example embodiment of a lead adapted to be steerable during insertion into an animal body, the lead comprises:

a structure that is substantially defined by at least one principal planar surface; the structure having a proximate end and a distal end; the structure comprised of a tip portion and a body; the tip portion on a distal end of the structure;

at least an electrode connected with the structure;

the tip portion is flexible in a direction that is substantially parallel to the principle planar surface whereby the shape of the tip portion is changeable during insertion of the lead into an animal such that the lead can move in a desired direction.

Another aspect of the example embodiment further includes a first means for changing the shape of the tip portion during insertion into an animal whereby the lead moves in a desired direction.

Another aspect of the example embodiment, the tip section has an about V shape with a left side and a right side; the lead providing a means for changing the shape of the tip by an operator controlled alteration of the length of the left side or right side of the tip section during the insertion of the lead.

Another aspect of the example embodiment, the lead further comprises at least one fluid chamber in at least the tip portion and at least one passage; whereby inflating or deflating the fluid chamber changes the shape of the tip section.

Another aspect of the example embodiment, the lead further comprises at least one control wire passing through at least a channel extending from of the body to the tip portion; a distal end of the control wire positioned in the tip portion wherein extending and/or retracting a control wire changes the shape of the tip portion.

Another aspect of the example embodiment, the lead further comprises a stylet passing through a channel in the body extending from at least portions of the body to the tip portion; the stylet having a bent or curved section within the tip section.

Another example embodiment is of a lead adapted to be steerable during insertion into an animal body, the lead comprises:

a structure that is defined by at least one principal planar surface; the structure having a proximate end and a distal end; the structure comprised of a tip portion and a body; the tip portion on a distal end of the structure;

at least an electrode connected with the structure;

the tip portion is flexible in a direction that is substantially parallel to the principle planar surface;

at least one fluid chamber in at least in the tip portion wherein the volume of the fluid chamber can be changed to change the shape of the tip section.

Another example embodiment is of a lead that is capable of percutaneous insertion, the lead comprising:

a structure having a proximate end and a distal end; the structure is substantially defined by at least one planar surface; the structure comprised of a tip portion and a body; the tip portion on a distal end of the structure;

at least an electrode connected with the body;

the tip portion is flexible in a direction that is substantially parallel to the planar surface;

at least one control wire passing through at least a channel extending from the body to the tip portion;

a distal end of the control wire positioned in the tip portion wherein extending and/or retracting a control wire changes the shape of the tip portion.

Another example embodiment is of a percutaneous insertion-capable lead, the lead comprising:
  a structure having a proximate end and a distal end; the structure comprised of a tip portion and a body; the tip portion on the distal end of the structure; the structure is a paddle structure being substantially defined by two principal opposing planar surfaces;
  a conductor of the plurality of conductors electrically couples one terminal of the plurality of terminals with at least one electrode of the plurality of electrodes; the tip portion is flexible in a direction that is substantially parallel to the principle planar surfaces of the body; and
  a stylet passing through a channel in the body extending from portions of the body to the tip portion.

Another example embodiment is of a needle for medical use comprised of:
  a needle having a shaft and a tip section; an opening in the shaft; a lumen communicating with the opening and a plurality of holes in the tip section.

An aspect of the example embodiment is wherein the shaft has a circular horizontal cross section at least near the tip section; the tip section has a superior face and an inferior face; the area of the superior face is about 50% of the area of the tip section; and the area of the inferior face is about 50% of the area the tip section; and the tip section has a blunt tip.

An aspect of the example embodiment is wherein the tip section has a non-circular horizontal cross sectional shape; a front edge in the tip section defined by the intersection of the superior and inferior faces and the intersection of an asymmetric axis; a plurality of holes in the superior face and on an upper portion of the inferior face adjacent to the front edge.

Another example embodiment is a method of introducing solid or fluid in a human; the method comprising the steps of:
  percutaneously accessing a site proximate to a desired placement site though formation of an access passage using a needle and overlying sheath; the sheath having a sheath lumen;
  removing the needle while leaving the sheath in place; and
  introducing solid or fluid thru the sheath into the human or inserting a lead thru the sheath and directing the lead further through a human's tissue to the desired placement site.

An aspect of the example embodiment is wherein the method further comprises:
  the needle further comprises a needle having a shaft and a tip section; an opening in the shaft; a lumen communicating with the opening and a plurality of holes in the tip section and inserting the needle and sheath in the human to access the epidural space and sensing the tip of the needle reaching the epidural space by the loss of resistance technique;
  removing the needle;
    inserting the lead thru the sheath lumen and directing the lead further through the epidural space to the desired lead placement site; and
    removing the sheath.

Another aspect of the example embodiment method is using any of the example embodiment needles, needle assemblies, sheaths and leads in any combination.

The above and below advantages and features are of representative example embodiments only, and are not exhaustive and/or exclusive. They are presented only to assist in understanding the invention. It should be understood that they are not representative of all the inventions defined by the claims, to be considered limitations on the invention as defined by the claims, or limitations on equivalents to the claims. For instance, some of these advantages may be mutually contradictory, in that they cannot be simultaneously present in a single embodiment. Similarly, some advantages are applicable to one aspect of the invention, and inapplicable to others. Furthermore, certain aspects of the claimed invention have not been discussed herein. However, no inference should be drawn regarding those discussed herein relative to those not discussed herein other than for purposes of space and reducing repetition. Thus, this summary of features and advantages should not be considered dispositive in determining equivalence. Additional features and advantages of the invention will become apparent in the following description, from the drawings, and from the claims.

BRIEF DESCRIPTION OF THE DRAWINGS

The features and advantages of devices according to the present invention and further details of processes of using such devices in accordance with the present invention will be more clearly understood from the following description taken in conjunction with the accompanying drawings in which like reference numerals designate similar or corresponding elements, regions and portions and in which:

FIG. 1A-1 shows a cross sectional view thru the tip portion of the lead 20 shown in FIG. 1A.

FIG. 1A-2 shows a cross sectional view thru the body 30 of the lead 20 shown in FIG. 1A.

FIG. 1A-3 shows a longitudinal cross sectional view thru the tip portion 23 and body 30 of the lead 20 shown in FIG. 1A.

FIG. 7A shows a bottom up view of the needle shown in FIGS. 7A through 7E according to an example embodiment.

FIG. 7B shows a vertical longitudinal cross sectional view of the needle shown in FIGS. 7A through 7E according to an example embodiment.

FIG. 7C shows a top down view of the example embodiment's needle showing the superior face, holes in the tip section and sheath according to an example embodiment.

FIG. 7D shows a transverse cross sectional view through the tip section according to an example embodiment.

FIG. 7E shows a front end view of the tip section and a lower bottom face of the sheath according to an example embodiment.

FIGS. 8A thru 8D show an example method for placing a lead in an epidural space.

FIG. 8A shows a cross sectional view that illustrates the placement of the needle and sheath into the epidural space according to an example embodiment.

FIG. 8B shows the needle withdrawn from the sheath according to an example embodiment.

FIG. 8C shows a probe being used according to an example embodiment.

FIG. 8D shows the placement of a lead according to an example embodiment.

DESCRIPTION OF THE EXAMPLE EMBODIMENTS

The example embodiments of the present invention will be described in detail with reference to the accompanying drawings. The example embodiments provide needle, sheath and lead devices and methods using the same.

Figure 1A:
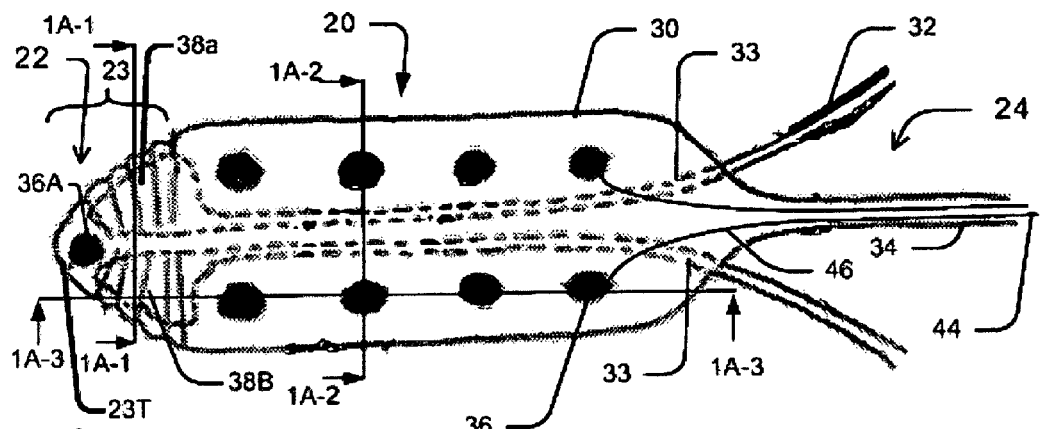
FIG. 1A shows top down view of an example embodiment of a flex tip lead with fluid chambers.

The example embodiment leads can be adapted to be steerable during insertion into an animal body. Three example embodiments are shown in FIGS. 1A (e.g., fluid chamber(s)), 3A (e.g., control wire(s)) and 4A (e.g., bent stylet). The shapes of the tip sections of the leads are changeable during use or insertion into an animal body so that the lead can move in a desired direction.

Figure 5A:
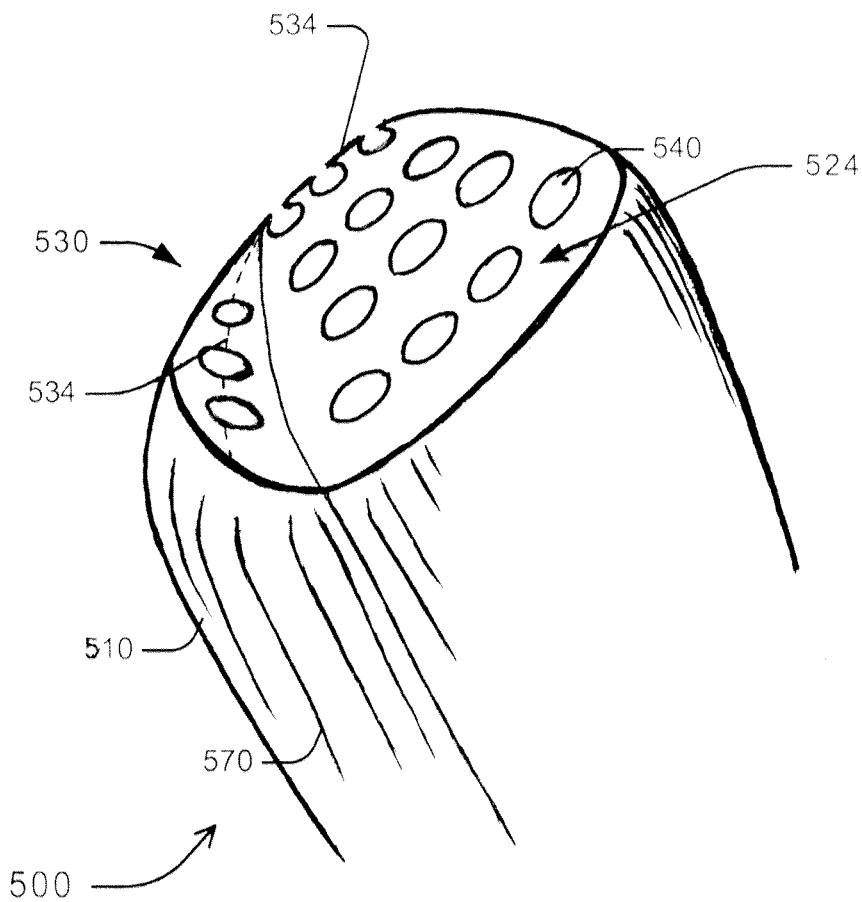
FIG. 5A shows a three dimensional view of an example embodiment of a needle and sheath of the invention.

The example embodiment needles have plurality of holes in a tip section. Two example embodiment needles and sheaths are shown in FIGS. 5A and 7E.

Example embodiment methods are provided for using any combination of the example embodiment needles, sheaths and/or leads. See e.g., FIGS. 8A to 8E.

Below the example embodiments of the leads are described. Next, the example embodiments for the needle and sheaths are presented. Then example embodiment methods are discussed.

Example Embodiment Leads

I. Flex Tip Lead with Fluid Chambers

FIG. 1A shows an example embodiment of a flex tip lead with fluid chambers 38A 38B. The lead can be a percutaneous insertion-capable lead having a plurality of electrodes, such lead is able to pass through a percutaneous introduction structure and adapted for to be steerable during insertion into an non-human or human animal body at a precise location. The shape of the tip portion is changeable (e.g., change the shape of the tip section—one side of tip section is longer than the other side) during insertion into an animal whereby the lead can move in a desired direction.

The lead can comprise: a lead structure 20 that can be substantially defined by one principle plane or two principal opposing planar surfaces, a sheath 34 and terminals 44. The lead structure 20 can have various shapes, such as a curved shape to match the curve of the dura, or an about flat bottom surface (facing the spine) and an irregular top surface.

The structure 20 has a proximate end 24 and a distal end 22. The structure is comprised of a tip portion 23 and a body 30. The tip portion 23 is on a distal end 22 of the lead structure. The tip section 23 can have a blunted tip 23T.

A shoulder area is needed on either side to establish the sharper tip. This is made with some redundant silicon-like soft material, so that extendibility is afforded. Extending one side would effectively cause the two shoulders to become asymmetrical, and the tip of the lead being closer to one side (the nonextended side). This will likely cause the lead preferentially moving to one side (non-extended side) while being advanced within the epidural space. With this design, the operator will be able to have control over the direction of the lead advancement by extending one of the lead shoulders.

The idea of percutaneously insertion of paddle lead to epidural space is a great improvement of neurostimulation technique and strategy; however, there are technical difficulties when putting the idea into practice. One major concern is the ability to advance the paddle lead within the epidural space for a course of about 20 centimeter or even longer (typically from higher lumbar level, where the needle is inserted, to mid thoracic level, the "sweet spot" for low back pain and lower extremity radiculopathy, or even to cervical level for disease entities involving cervical spine and upper extremities). What is even more critical is the ability to direct the lead's course of advancement so that it will stay posterior in relation to the spinal cord-which will ensure stimulation of dorsal column, not other parts of the spinal cord.

The lead structure 20 can be comprised of a medical grade, substantially inert material, for example, polyurethane, silicone, or the like. Such material should be non-reactive to the environment of the human body, provide a flexible and durable (i.e., fatigue resistant) exterior structure for the components of lead, and insulate adjacent terminals 44 and/or electrodes 36. Additional parts (e.g., a nylon mesh, a fiberglass substrate, or a support stylet/wire) (not shown) can be internalized within the lead structure to increase its overall rigidity and/or to cause the structure to assume a prescribed cross-sectional form.

Electrodes and Conductors

In an option, one (e.g., the ventral surface—the bottom surface designed to face a patient's spine) planar surface incorporates a plurality of electrodes 36. A conductor of the plurality of conductors 46 (only a few conductors are shown in FIG. 1A, conductors can individually connect to all electrodes) electrically couples one terminal of the plurality of terminals 44 with at least one electrode of the plurality of electrodes 36.

The electrodes 36 can be connected by conductors that end in terminals 44. Also, each electrode contact can have its own wiring structure all the way to the tail of the lead, and can have its own connection to the battery system. The electrodes can be individually managed or controlled so that all the settings of each electrode can be individually adjusted, including, but not limited to, turning on and off, frequency, voltage, current.

Tip Portion and Chambers

As show in FIG. 1A, two fluid chambers 38A 38B are in the tip portion 23.

Two passages 33 extending from the proximate end of the body to the tip portion. The passages 33 can be in communication with corresponding fluid chambers 38. In an embodiment, the chambers are about centered vertically above and below the anterior-posterior (e.g., coronal or frontal plane) plane of the body.

The tip portion 23 can be flexible in a direction that is substantially parallel to the principle planar surface(s) of the body. For example, as shown in FIG. 1C, the tip portion 23 moves laterally (e.g., left 23B) with respect to the body 30. In an option, the lead is adapted so that tip changes shape only in a horizontal direction (parallel with a plane of the lead) and not substantially in a vertical direction. Extending one side of the tip portion would make the two tip sides asymmetrical and the tip would be closer to one side (the non-extended side). Also, the chamber 38B could be aspirated or under vacuum or reduced pressure compared to the opposing chamber 38a. Note, that the tip portion can be flexible in other directions other than the parallel plane, for example the tip portion could flex up and down. The lead and the tip section can be adapted so that when the volume of a fluid chamber is changed to change the shape of the tip section 23 so that the blunted tip 23T moves to the left or right only in a direction substantially parallel to the principal planar surface. The chambers can be configured so that they do not expand significantly in the vertical direction and only expand/contract in the lateral (side) directions.

If the lead was inserted into an animal body, such as a human epidural space, this asymmetrical tip would cause the lead to move during insertion/positioning to the non-extended tip portion side. With this lead design the operator will be able to control the direction of the lead advancement by extending or shortening one side of the tip portion.

The tip section proximate the chambers can have an accordion like structure. See for example cross sectional FIG. 1A-3. The folds or wrinkles can be vertically aligned. The folds or wrinkles 27 can form an arc to the center of the lead. The chamber walls can be comprised of a redundant material that can be organized in accordion shaped folds.

The thickness of the walls of tip section around the chambers can vary to help the tip section bend in the principle plane.

There may be other tip section structures that enable flexing by increasing or decreasing the pressure in the chambers and the embodiments are not limited to these methods.

The tip portion can be made of a soft silicon like material with redundancy, organized in accordion-like pattern with or without the fluid chambers inside.

The tip section is preferably tapered and is preferable not a semicircular shape. The lead tip can have a V or conical shape and can have a blunted or rounded front end. In an aspect, the tip is blunted so to be not too sharp so that the tip will not puncture the dura matter during insertion.

The body 30 should have an appropriate rigidity for proper insertion. The body 30 can contain support structures (removable or non-removable) to add more rigidity. For example a support wire 48 can be inserted in the center of the body (for example see (FIG. 1F). The support wire 48 can be used in any of the lead embodiments of the present invention. The support wire 48 can extend into the tip portion for all lead embodiments (see for example FIG. 1G).

Overview of FIGS.

Figures 1, 1A:
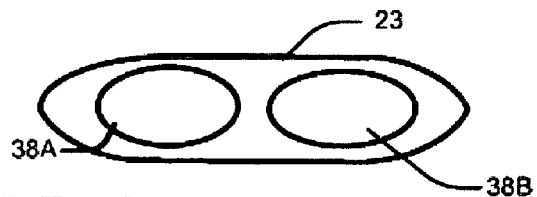

FIG. 1A-1 shows a cross sectional view thru the tip portion of the lead 20 shown in FIG. 1A.

Figures 1, 1A, 2:
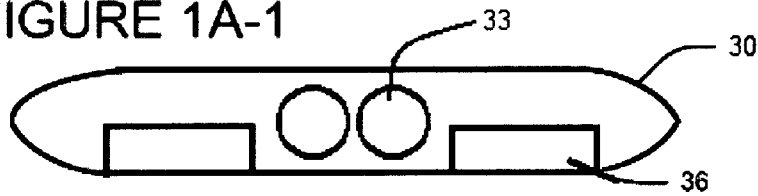
Figures 1, 1A, 2, 3:
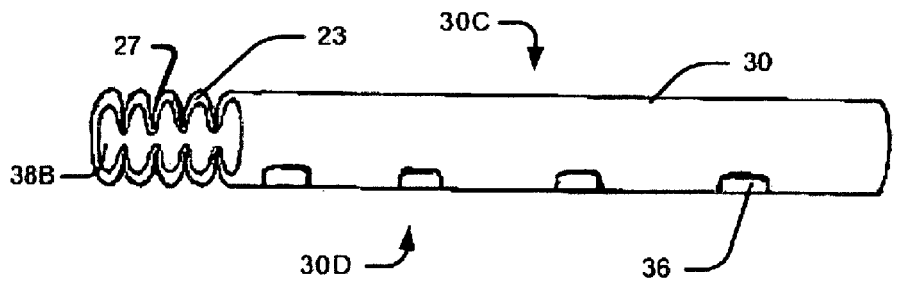

FIG. 1A-2 shows a cross sectional view thru the body 30 of the lead 20 shown in FIG. 1A.

FIG. 1A-3 shows a longitudinal cross sectional view thru the tip portion 23 and body 30 of the lead 20 shown in FIG. 1A. The lead structure 20 that is substantially defined by two principal opposing planar surfaces (ventral surface) 30C (dorsal surface) 30D.

Figure 1B:
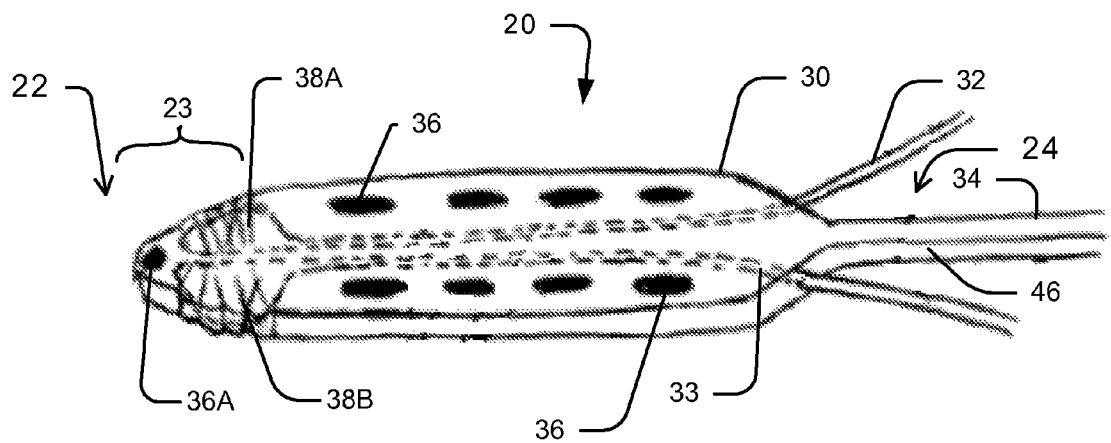
FIG. 1B shows a three dimensional view of the lead shown in FIG. 1A according to an example embodiment.
Figure 1C:
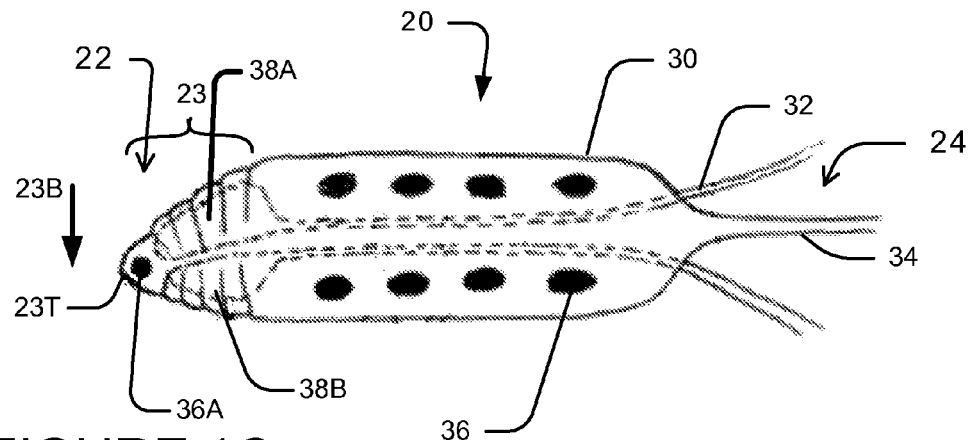
FIG. 1C shows a top down view of the lead shown in FIG. 1A with the tip moved to the left according to an example embodiment.

FIG. 1B shows a three dimensional view of the lead shown in FIG. 1A.

FIG. 1C shows a top down view of the lead shown in FIG. 1A with the tip moved to the Left.

Figure 1D:
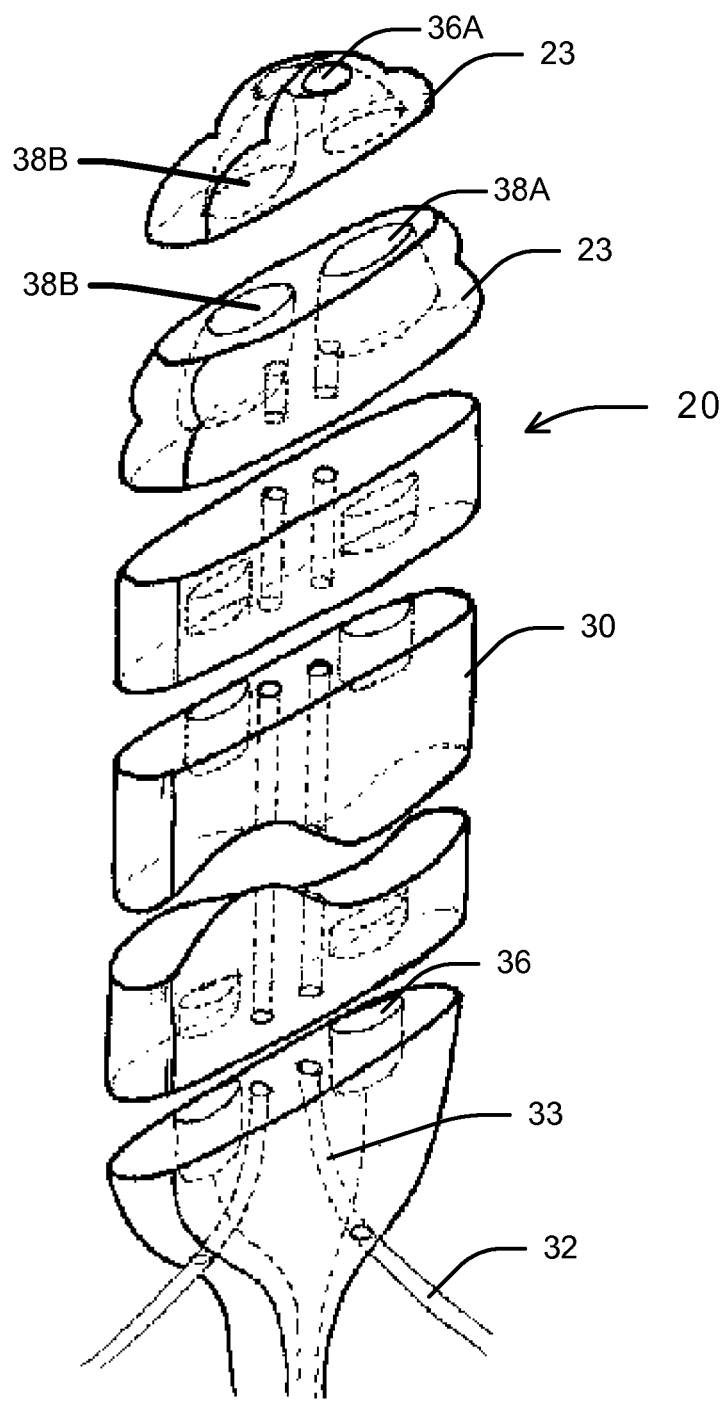
FIG. 1D shows a sectioned three dimensional view of an example embodiment of the lead shown in FIG. 1A.

FIG. 1D shows a sectioned three dimensional view of an example embodiment of the lead having two fluid chambers and passages 33 in a medial (e.g., central) part of the body as shown in FIG. 1A.

Figure 1E:
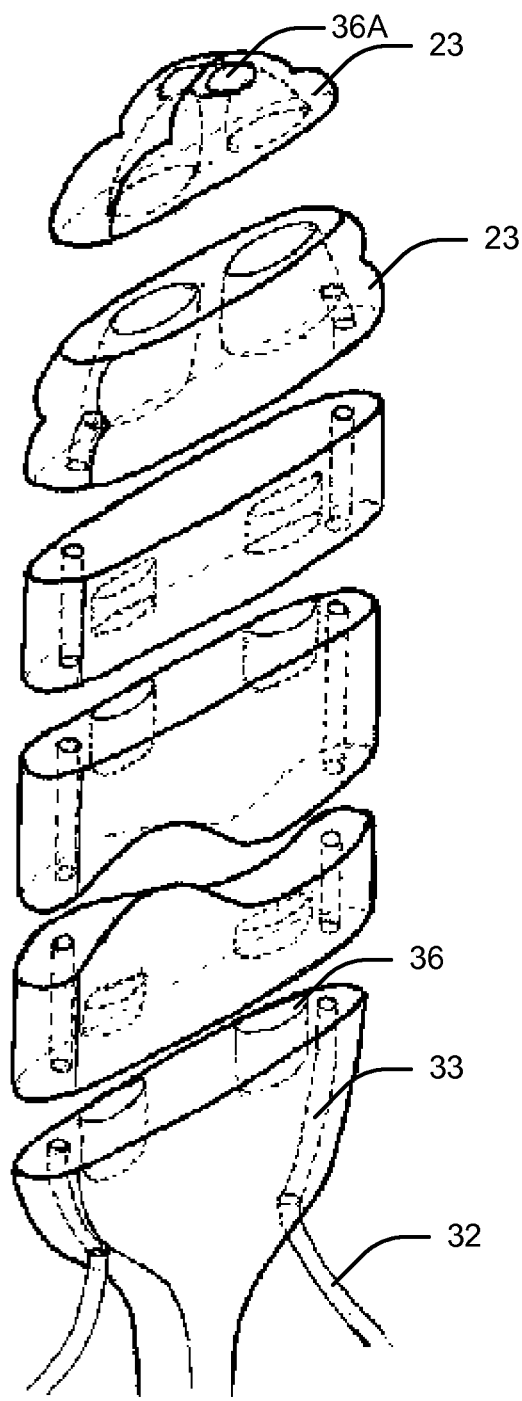
FIG. 1E shows a sectioned three dimensional view of another example embodiment of the lead
Figure 1F:
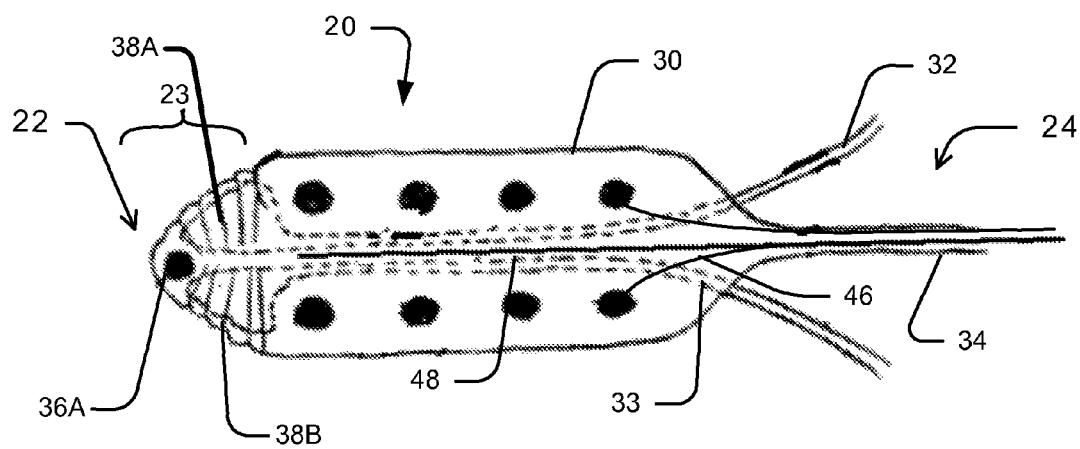
FIG. 1F shows a channel longitudinally extends thru at least a portion of the body 30 and is adapted to fit a stylet according to an example embodiment.

FIG. 1E shows a sectioned three dimensional view of another example embodiment of the lead having two fluid chambers and the passages 33 pass thru a lateral (outside) section of the body 30.

FIG. 1F shows a channel longitudinally extends thru at least a portion of the body 30 and is adapted to fit a stylet 48. The stylet preferably does not interfere with the flexing of the tip section 23.

The stylet can be used to help push or insert the lead into place. The stylet can be removable after insertion of the lead in the treated animal.

Figure 1G:
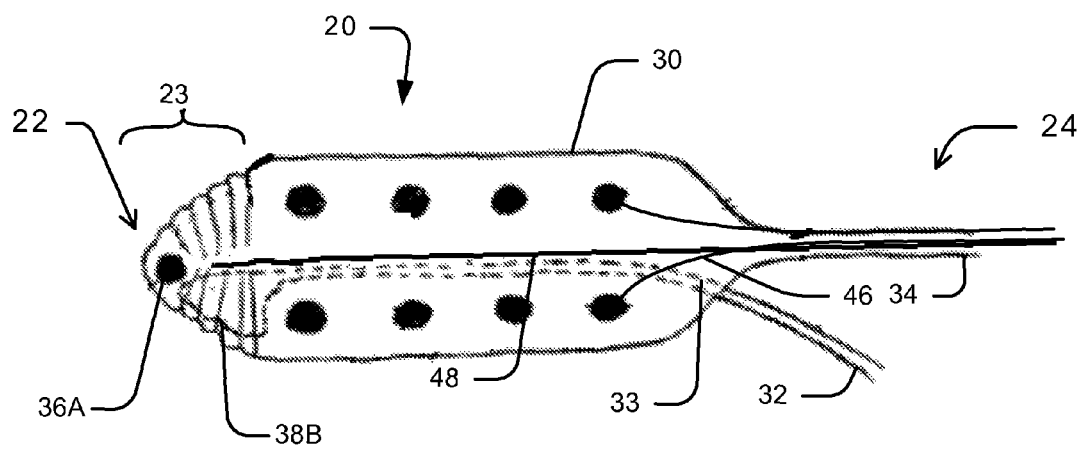
FIG. 1G shows an embodiment with one chamber according to an example embodiment.

FIG. 1G shows an embodiment with one chamber 38B, one passage 33 and one tube 32. FIG. 1G also shows the optional stylet 48.

The one chamber 38B can be expanded with a pressure increase or compressed with a vacuum or aspiration. The other side (right side) of the tip can compress or expand even though there is no right side chamber because of the elasticity of the tip section and stress/strain from the chambered left side.

Devices for Expanding and/or Contracting the Fluid Chambers

A device for expanding and/or contracting the fluid chambers (e.g., changes of pressure in, and/or volume of, the chambers by increasing or reducing the amount of fluid in the chambers) can be attached to the tubes 32. For example a syringe could be attached to the tubes 32 that is in communication with the passage(s) 33.

The outer body of the lead structure 20 can be manufactured from a material that is biocompatible and electrically insulating.

Tip Marker at the Tip of Lead

FIG. 1A shows a tip marker (e.g., tip electrode, palette) 36A proximate to the distal end (tip of the tip section 23). The tip marker 36A is observable using an imaging technique (e.g., Fluoroscopy) in an animal body.

The tip marker 36A on the tip 23T of tip portion 23 can be used to show the direction of where it is moving to in real time under x-ray during insertion.

The tip marker can function as an electrode also at the same time.

Pattern of Electrodes

Figure 2A:
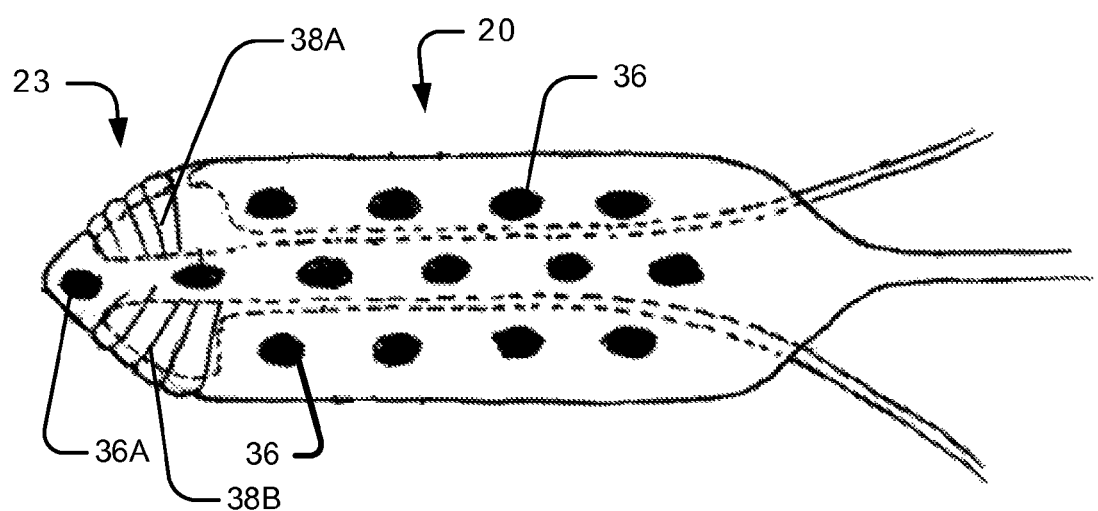
FIG. 2A shows an example embodiment lead with a 3 column configuration of electrodes.

Electrodes (e.g., contacts) can be arranged in many configurations such as in multiple columns and configured in many different ways. For example FIG. 1A shows a 2 column configuration. and FIG. 2A shows a 3 column configuration.

II. Flex Tip Section Lead with at Least One Control Wire

Figure 3A:
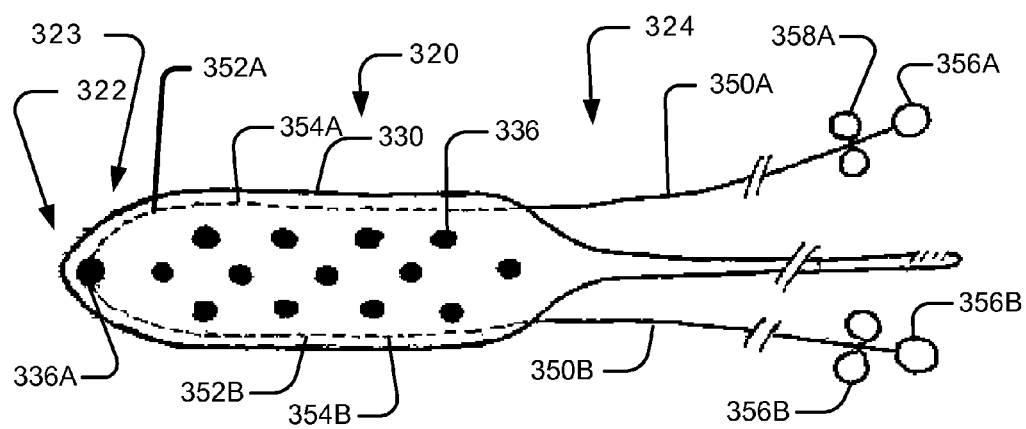
FIG. 3A shows top down view of an example embodiment of a lead having at least two control wires.
Figure 3B:
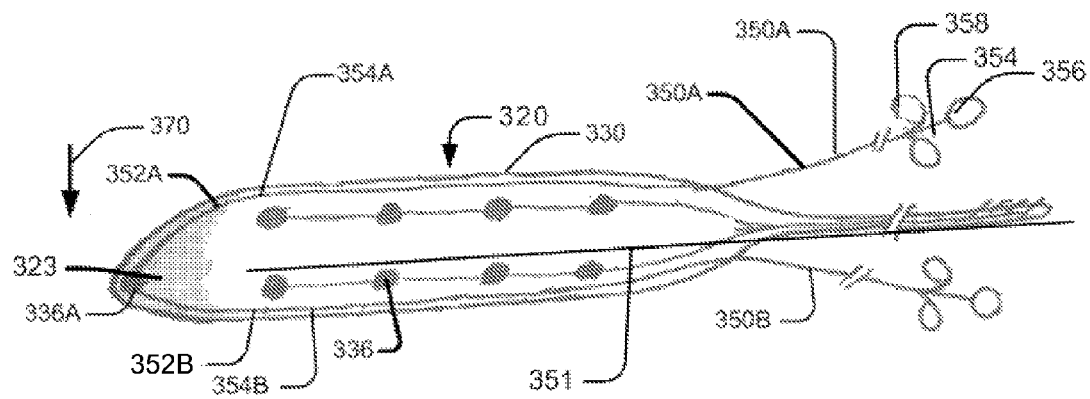
FIG. 3B shows top down view of an example embodiment of a lead having at least one control wire and an optional support stylet.
Figure 3C:
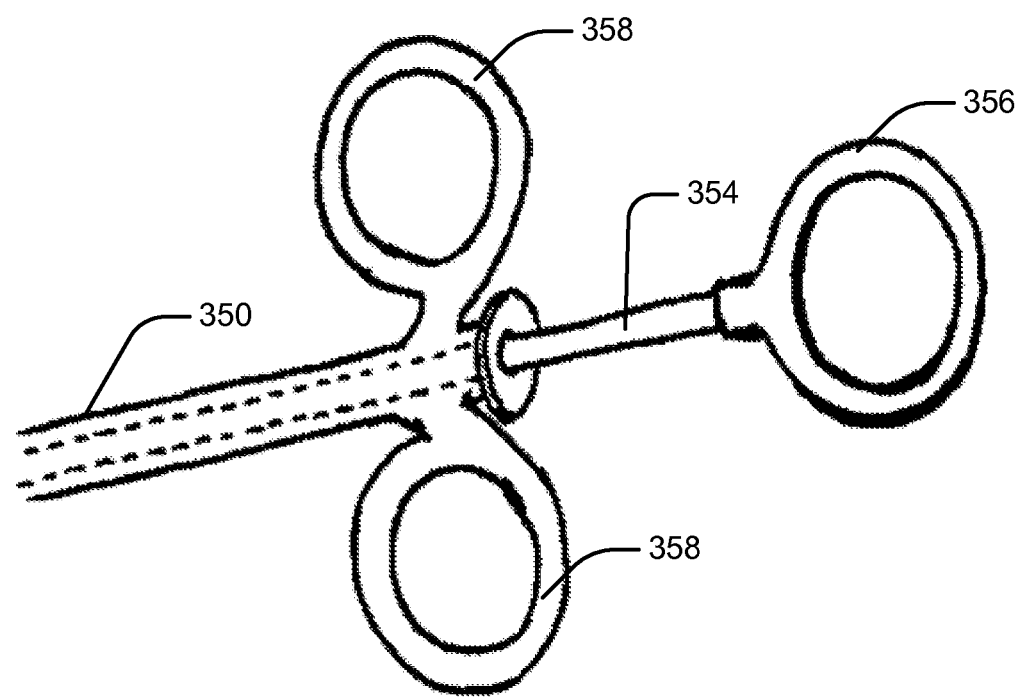
FIG. 3C shows a three dimensional view of the ends of the two of the control wires extending out of the tubes which can be connected with tube handles according to an example embodiment.

FIGS. 3A and 3B show an example embodiment of a lead having at least two control wires 354A 354B that can be used for positioning the lead during insertion. FIG. 3G shows an example embodiment of a lead having one control wire.

The percutaneous insertion-capable lead can comprise a lead structure 320 having a proximate end 324 and a distal end 322. The structure 320 is comprised of a tip portion 323 and a body 330. The tip portion 323 on a distal end 322 of the structure 320.

A conductor of the plurality of conductors electrically couples one terminal of the plurality of terminals with at least one electrode of the plurality of electrodes (not shown). The electrodes 336 can have many configurations as described above. The electrodes can be connected to terminals by conductors as described above.

The tip portion 323 can be flexible in a direction that is substantially parallel to a plane. The tip portion is comprised of a flexible material. The tip portion is more flexible than the body. The body should be more ridge to help thread thru a conduit and animal body.

Two control wires 354A 354B can pass through two spaced channels 352A 352B extending from the proximate end of the body 330 to the tip portion. Two control wires preferably pass through two spaced channels 352A 352B extending from the proximate end of the body 330 to the tip portion 323.

The control wires 354A 354B can be removably anchored in the tip portion 323 wherein extending and/or retracting a control wire 345A 354B changes the shape of the tip portion 323.

The tip portion is made of biomaterial of high elasticity.

Paddle Structure Lead

In an option, the structure 330 is a paddle structure having substantially defined by two principal opposing planar surfaces. One of the two planar surfaces incorporates the plurality of electrodes 336 (similar to as shown in FIG. 1A-2). As shown in FIG. 3B, the tip portion 323 can be flexible in a direction (370) that is substantially parallel to the principle planar surfaces of the body 330.

FIG. 3B shows the tip section is bent to the left (370) in a direction parallel to the planar surfaces. The tip section can have about V-shape. The tip section has a left and a right side. As shown in FIG. 3B, when the tip is bent to the left, the right side of the tip section lengthens and the left side shortens.

FIG. 3B also shows an aspect where the body 330 should have an appropriate rigidity for proper insertion. The body 330 can contain support structures (removable or non-removable) to add more rigidity. For example a removable support wire 351 can be inserted in the center of the body.

Bending Devices

The lead can further comprise a bending means for flexing the tip portion in an angle preferably parallel with the planar surfaces by manipulating the control wires 354A 354B. For example, two control wires can be placed on the sides of the lead and by pushing one wire, one side of the tip portion is extended, causing the distal part of the tip moving towards the opposite side (in a angle perpendicular to the planar surfaces), as shown in FIG. 3B.

Tubes 350A 350B can encircle the control wire 345A 354B as the wire exits from the channels 352A 353B. The two tubes 350A 350B can communicate with the two channels 352A 352B. As shown in FIGS. 3B and 3C, the ends of the two of the control wires 354A 354B away from the channels 352A 352B extending out of the tubes 350A 350B which can be connected with tube handles 358A 358B (ring(s) at the end of tubing). A ring-like structure 356 or other holding device can be placed on the end of the wire 354. The majority part of the channels 352A and 352B within the lead body 330, but not within the tip portion 323, is not distendable (not made of material with high elasticity) in the longitudinal axis. The two tubes 350A and 350B are not made of material to allow distendability in the longitudinal axis. The tip portion 323 is made of highly elastic biomaterial, therefore this part of the channels 352A and 352B is distendable (e.g., stretchable).

Tip Marker

A tip marker 336A (e.g., palette, contact electrode) is located in the distal part of the tip portion. The tip marker 336A can have two dimples, one on each side. The distal ends of channels 352A and 352B communicate with the dimples to allow the distal ends of the control wires 354A and 354B seating within the dimples of the tip marker when being advanced. Advancing one wire on one side of the lead pushes the tip marker to the opposite side and extends the tip portion of the lead on the ipselateral side in the longitudinal axis. This is preferably parallel to the planar surfaces of the body. The ends of the control wires are detachable from the tip marker. The control wires can be removed from the lead after the lead is placed in the patient's body.

The tip marker (Palette) also can function as a stopper to stop the wires in the case of using wiring to change the shape of the tip. The tip marker could be any shape for that purpose, spherical etc. Preferably, as shown in FIGS. 3E and 3F, the tip marker 336A has two dimples on the sides. FIG. 3E, show a cylinder shape tip marker, but the tip marker can have other shapes such as a spherical shape with two dimples. The tip marker can also function as an electrode.

The tip marker 336 can have dimples 336D at two sides, which partially oppose each other at an angle between about 60 and 140 degrees. The dimples on the tip marker can seat the distal ends of the controlling wires when either or both controlling wires is/are advanced with force through the tube.

FIG. 3F is a cut away three dimensional view of the tip marker 336A shown in FIG. 3E.

Aspect—Control Wire on Lateral Sides of Body

Figure 3D:
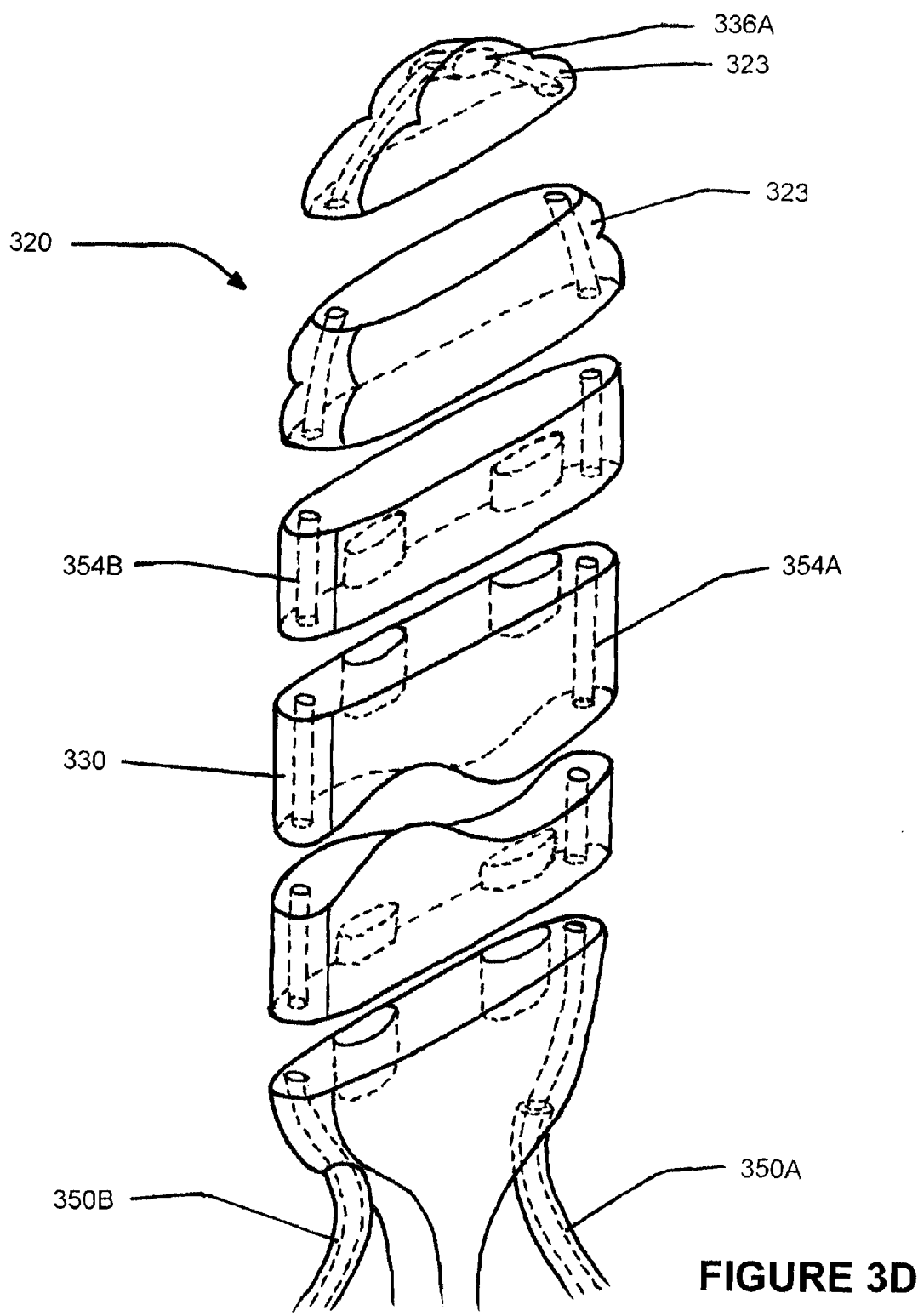
FIG. 3D, shows a three dimensional view of another aspect where in the control wires pass thru at least portion of the body toward the outer sides.
Figure 3E:
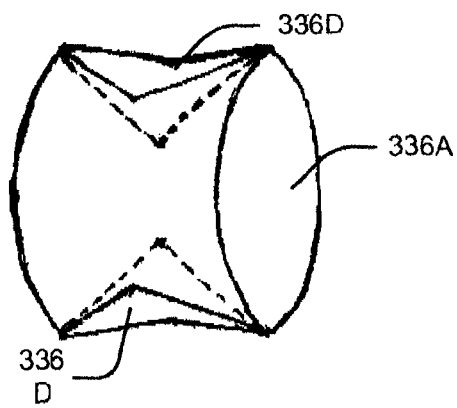
FIGS. 3E and 3F, show three dimensional views of a tip marker according to an example embodiment.
Figure 3F:
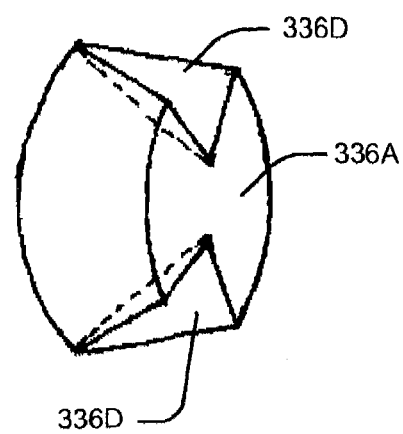
Figure 3G:
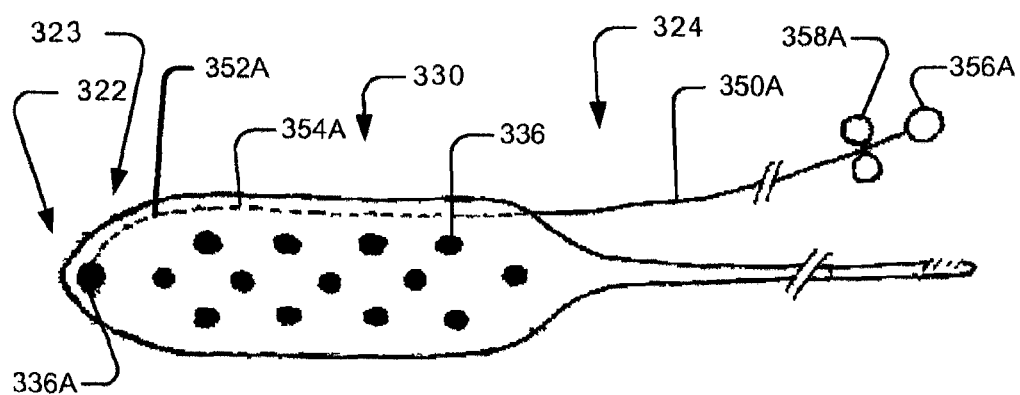
FIG. 3G shows an example embodiment of a lead having one control wire.

Referring to FIG. 3D, another aspect is shown where in the control wires 354A 354B pass thru at least portion of the body 330 toward the outer sides of the body.

III. Paddle Lead with Bent

Figure 4A:
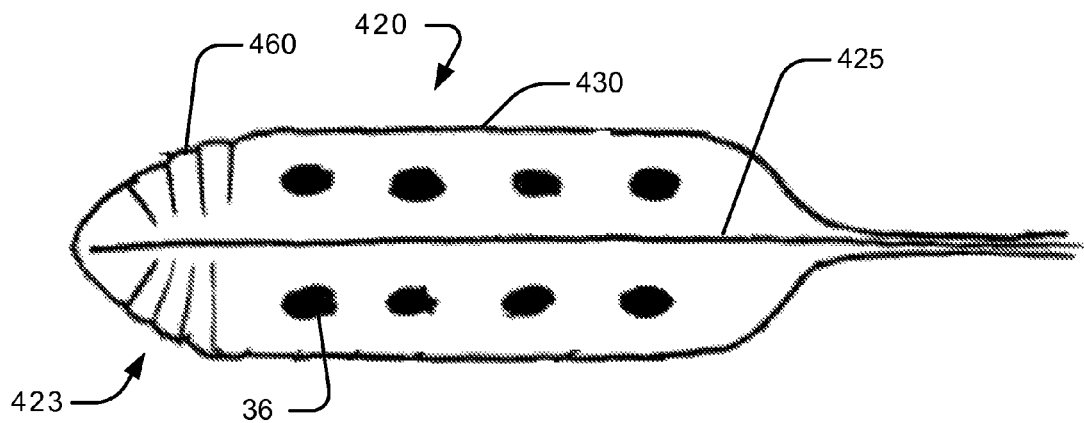
FIGS. 4A and 4B show top down views of an example embodiment of a percutaneous insertion-capable lead having a stylet.
Figure 4B:
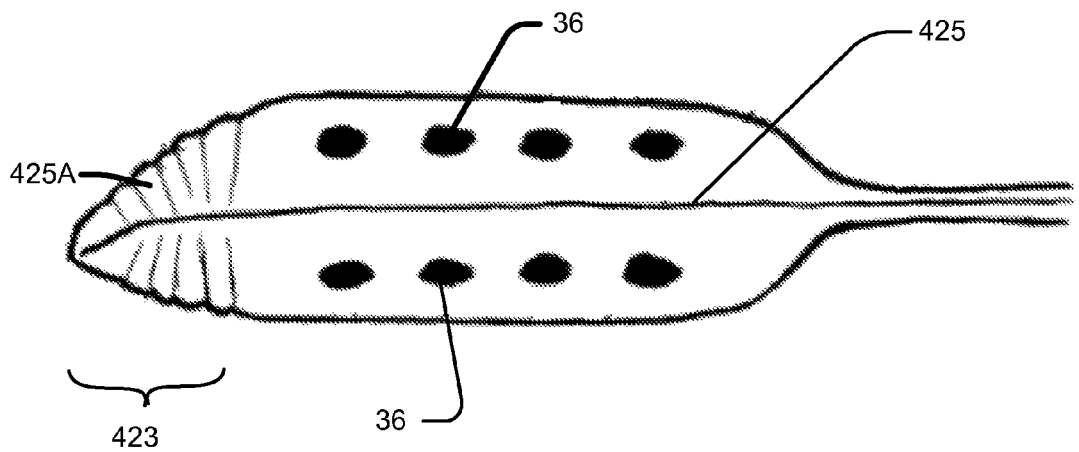

Referring to FIGS. 4A and 4B, an example embodiment is shown of a percutaneous insertion-capable lead 420 having a stylet 425.

The lead is comprised (FIG. 4A) of a lead structure 420 having a proximate end and a distal end. The structure is comprised of a tip portion 423 and a body 430. The tip portion 423 is located on the distal end of the structure.

The lead structure is a paddle structure having substantially defined by two principal opposing planar surfaces.

The lead structure has electrodes 36 connected to terminals by conductors similarly as described above and shown in FIG. 1A. The lead has a conductor of the plurality of conductors, electrically coupling one terminal of the plurality of terminals with at least one electrode of the plurality of electrodes.

The tip portion 423 is flexible in a direction that is substantially parallel to the principle planar surfaces of the body.

Figure 4C:
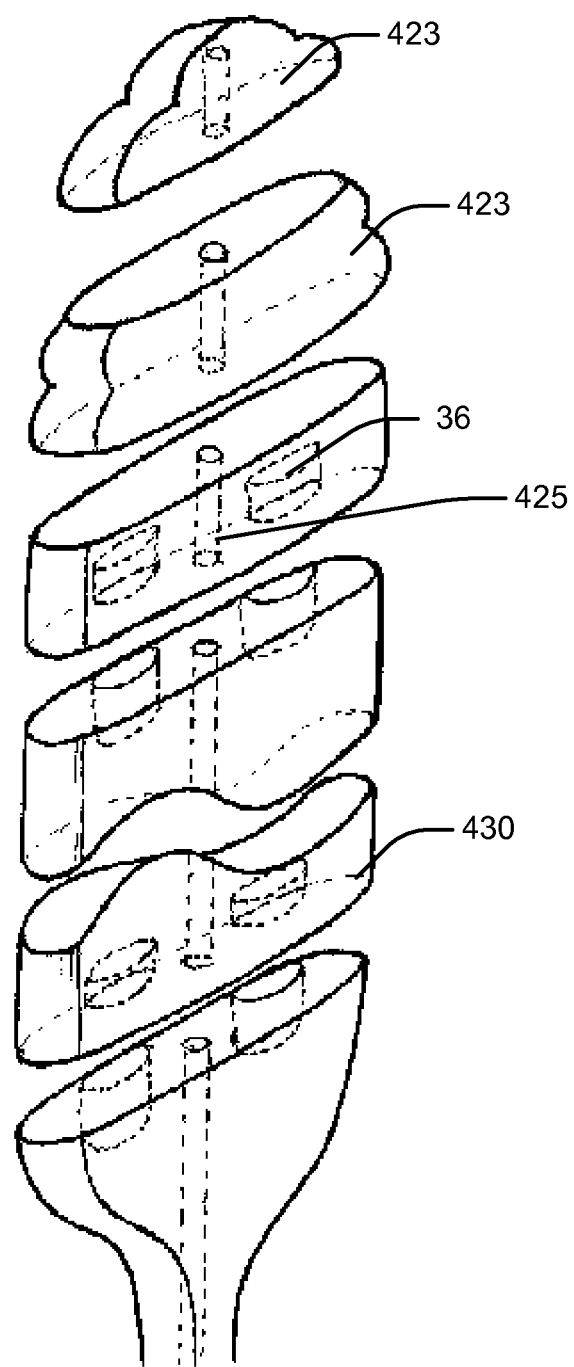
FIG. 4C shows a cut away three dimensional view of example embodiment of a percutaneous insertion-capable lead having a stylet.
Figure 4D:
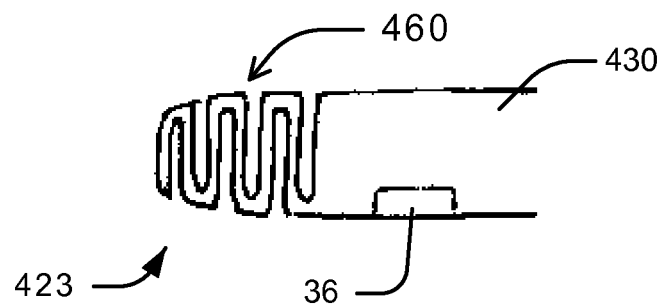
FIG. 4D is a cross sectional view of the accordion like folds in the tip section (similar to FIG. 4A) according to an example embodiment of the invention.
Figure 4E:
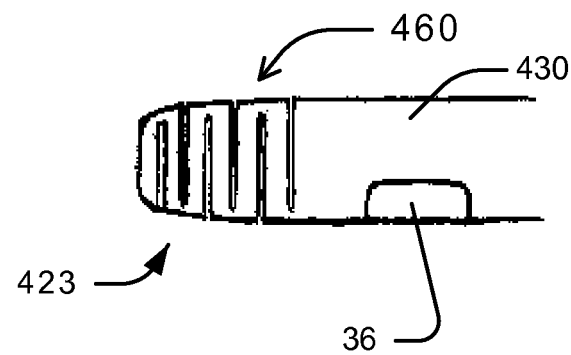
FIG. 4E is a cross sectional view of the accordion like folds in the tip section (similar to FIG. 4A) according to an example embodiment of the invention.

As shown in cross sectional view FIGS. 4D and 4E, the tip portion 423 can have accordion structures 460 where redundant tip material is arranged in folds. When a stylet or wire with bent tip is inserted, one side of the tip portion compress and other side expands (or unfolds). The tip portion can be made of elastic and redundant material which is arranged in accordion-like structure, affords the flexibility/expandability of the tip. FIG. 4E shows closer spacer folds 460 than FIG. 4D.

As shown in FIGS. 4A and 4B, the lead 420 has 1) a flexible/expendable tip portion 423 that tapers to a blunt point at far distal termination, preferably not a semicircular end.

FIG. 4C shows a cut away three dimensional view of example embodiment is shown of a percutaneous insertion-capable lead having a stylet.

A stylet 425 (wire) can pass through a channel in the body extending from portions of the body 430 to the tip portion.

The stylet may have bent or curved section 423A, when inserted, causes the tip section of the lead bent in the direction of the wire. Rotating the wire with the bent or curved tip caused the tip section of lead bent in a different direction.

The stylet can be bent or curved as shown in FIG. 4B. As an option, the stylet may be used in combination with other bending mechanisms and function to increase the rigidity of the lead structure thus facilitating lead insertion. The stylet can be removed after the lead is positioned in the proper place in the animal or patient.

The tip section of lead structure can have a tapered shape that is not semicircular. The tip section can have an about V shape with a blunted tip.

The stylet can be comprised of a metallic material with memory and the tip portion can be pre-bent at an angle between about 125 to 155 degrees.

The stylet can be rotated within the lead body in a human body during insertion so that the tip direction can change from left to right.

IV. Example Embodiments of Needles and Sheathes

Example embodiments of needles and conduit sheaths for medical use are provided.

FIGS. 5A thru 5H and FIGS. 6A to 6C show an embodiment of a needle having a plurality of holes in a tip section. The needle can have a non-circular cross section and the tip section can have an asymmetric shape. This lead and corresponding sheath can be used to insert a paddle style lead or a non-cylindrical lead.

FIGS. 7A to 7E show another example embodiment where the needle shaft can have a circular cross section and the tip can have a symmetric shape. This embodiment can be used to insert a circular lead or to introduce fluids or solids into an animal body.

Both example embodiment needles and sheaths can be used in the methods shown in FIGS. 8A to 8E.

A. Non-Circular Epidural Needle and Sheath

Referring to FIGS. 5A thru 5H and 6A thru 6C, there is shown in example embodiment of a needle for medical use.

FIGS. 5A thru 5H and FIGS. 6A thru 6C show at least the following elements: opening (back opening) 502, needle 500, tip section 520, shaft 510, lumen 504, mid horizontal longitudinal axis 506, asymmetric horizontal longitudinal axis 508, inferior face of tip section 530, superior face of tip section 524, front edge 534, sheath 570, conduit sheath distal opening (to expose distal part of needle tip section) 574, conduit sheath proximate opening 580, Needle hub 582, and conduit sheath channel 584.

Referring to FIG. 5A and FIGS. 5B thru 5H, a needle 500 for medical use is comprised of: a needle 500 having a shaft 510 and a tip section 520; an opening 502 (FIG. 6C) in the shaft; a plurality of holes 540 in the tip section 520, and a lumen 504 communicating with the opening 502 and a plurality of holes 540.

Figure 5B:
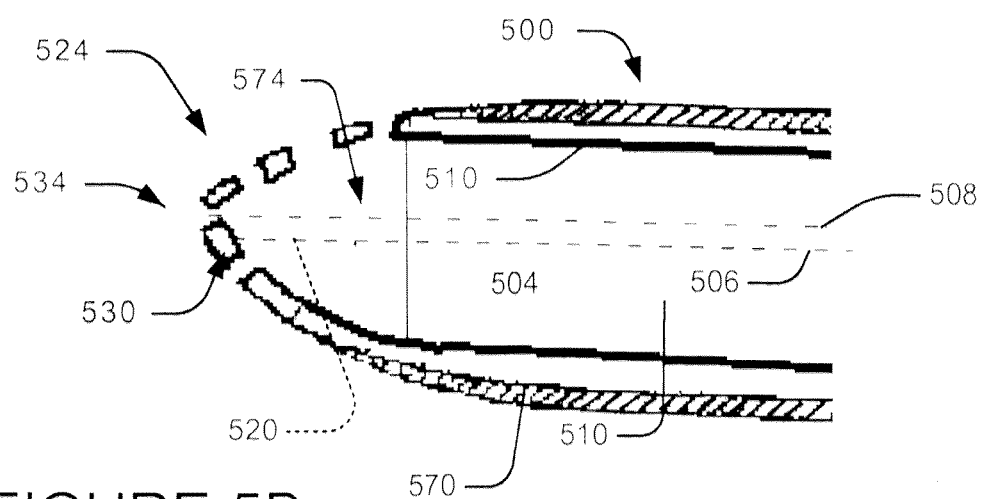
FIG. 5B shows a vertical longitudinal cross sectional view of the needle and sheath in FIG. 5A.
Figure 5C:
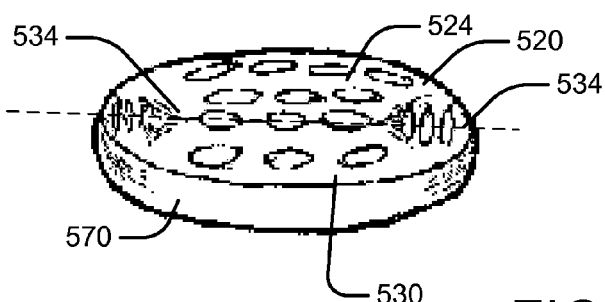
FIG. 5C shows a front end view of the tip section and a lower bottom face of the sheath that overlies a lower portion of the inferior face of the tip section.
Figure 5D:
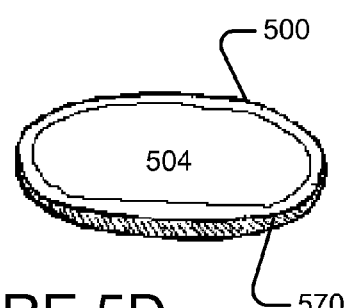
FIG. 5D shows a horizontal cross sectional view thru the needle tip section taken at a point where the sheath does not cover the superior face and covers a bottom portion of the inferior face.

In the example shown in FIG. 5D, the tip section can have a non-circular horizontal cross sectional shape, such as an about oval, or rectangular, round edge rectangular shape.

FIG. 5A shows a three dimensional view of an example embodiment of a needle 500 and sheath 570 of the invention. FIGS. 5H thru 6C show views of the needle 500 and sheath 570 shown in FIG. 5A FIG. 5B shows a vertical longitudinal cross sectional view of the needle and sheath in FIG. 5A.

FIG. 5C shows a front end view of the tip section 520 and a lower bottom face of the sheath 570 that overlies a lower (proximate) portion of the inferior face 530 of the tip section. The front edge 534 (e.g., front line, inferior/superior line) is the dashed dividing line between the inferior face and superior face.

FIG. 5D shows a transverse cross sectional view thru the needle tip section taken at a plane where the sheath does not cover the superior face but does cover a bottom portion of the inferior face 530.

Figure 5E:
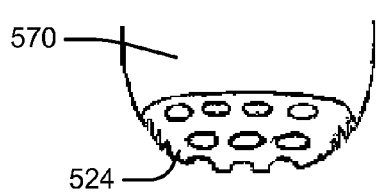
FIG. 5E shows a top down view of the needle shown in FIG. 5A.

FIG. 5E shows a top down view of the needle shown in FIG. 5A.

Figure 5F:
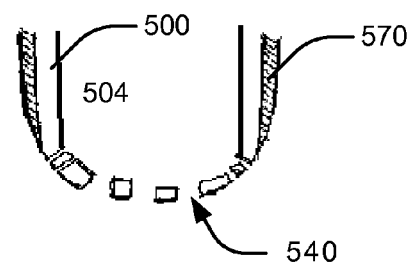
FIG. 5F shows horizontal longitudinal cross sectional view of the needle tip section, shaft and sheath.

FIG. 5F shows horizontal longitudinal cross sectional view of the needle 500 tip section 520, shaft 510 and sheath 570.

Figure 5G:
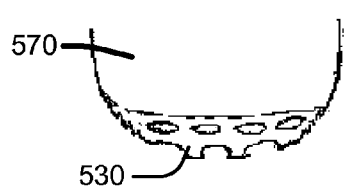
FIG. 5G shows a bottom up view of the needle shown in FIG. 5A.

FIG. 5G shows a bottom up view of the needle shown in FIG. 5A.

Figure 5H:
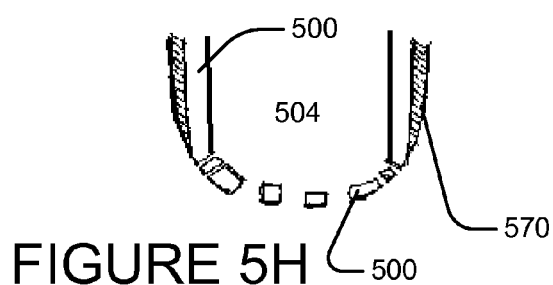
FIG. 5H shows horizontal longitudinal cross sectional view of the needle tip section, shaft and sheath.

FIG. 5H shows horizontal longitudinal cross sectional view of the needle 500 tip section 520, shaft 510 and sheath 570.

Figure 6A:
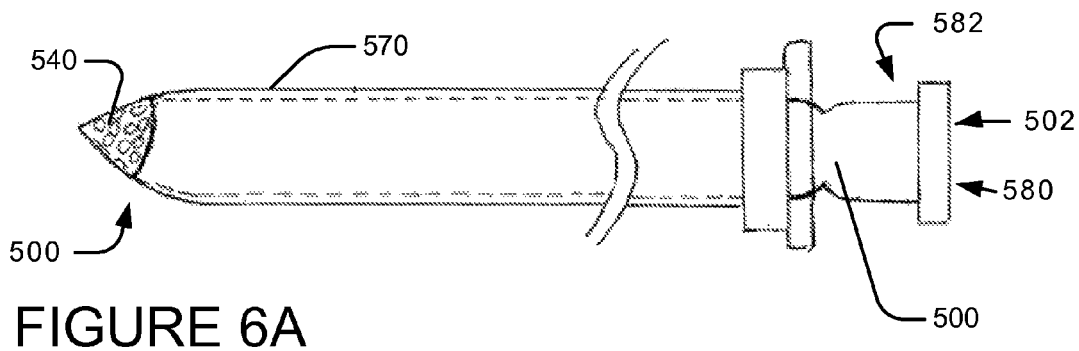
FIG. 6A shows a lateral (side) view of the needle in a sheath according to an example embodiment.

FIG. 6A shows a lateral (side) view of the Needle and sheath.

Figure 6B:
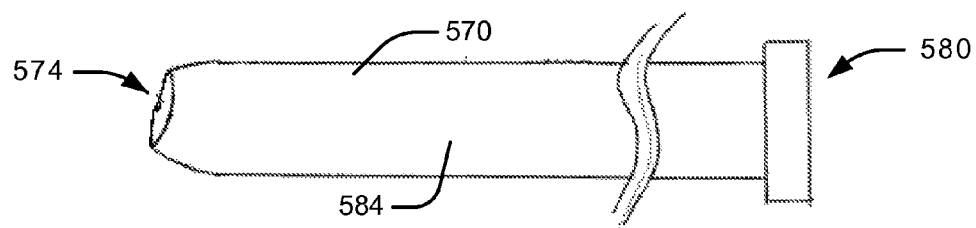
FIG. 6B is a lateral (side) view of the sheath according to an example embodiment.

FIG. 6B shows a lateral (side) view of the sheath.

Figure 6C:
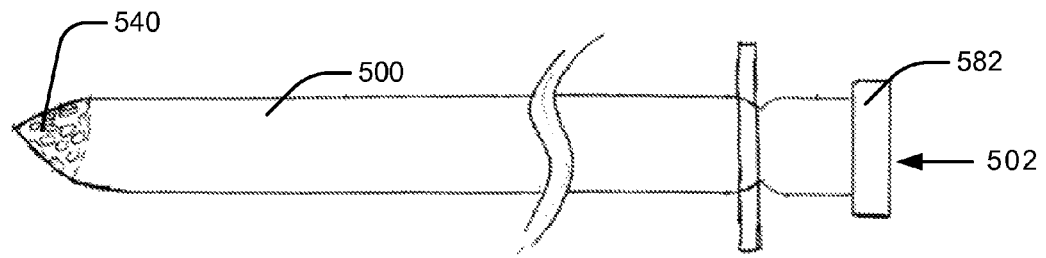
FIG. 6C is a lateral (side) view of the needle according to an example embodiment.

FIG. 6C shows a lateral (side) view of the needle.

Shape of Tip Section

In an aspect of the example embodiment, referring to FIGS. 5A thru 5H, a front edge 534 is defined by the intersection of the superior and inferior faces 524 530 and the intersection of an asymmetric plane 508.

Note that superior and inferior directions are relative. The superior face 524 is the tip face seen when looking down at the tip section with the needle in the orientation shown in the FIG. 5A The inferior face 530 is the face seen when looking up at the needle tip in the orientation show in the FIGS.

Referring to FIG. 5B, the asymmetric plane 508 is above a midline plane 506.

The tip is intentionally designed in an asymmetrical fashion, as demonstrated in FIG. 5B. This design will allow the overlying sheath having a skewed opening with the hole angled more towards superior direction, it will also make an initial penetrating opening at ligamentum flavum (at the moment the far distal end of the needle tip piercing through the ligament) which is more superior in relation to the needle/sheath path and the distal sheath opening. Both of the two facts will facilitate directing the lead structure preferentially moving/turning to the superior direction (refer to methods section, FIGS. 8A-8E).

In an aspect, the area of the superior face is less than 50% of the total tip portion area and the area of the inferior face is more than 50% of the total area of the tip portion. The tip section can have an asymmetric shape.

In an aspect, more than 50% of the holes 540 (or hole area) are in the superior face and less than 50% of the holes (or hole area) are in the inferior face.

A proximal portion of the inferior face of the needle tip can be covered by the overlying sheath, As shown in FIGS. 5A, 5B and other FIGS., the needle front edge 534 intersects at least one hole of the plurality of holes. An advantage of having at least one hole 540 in the far distal edge of the tip or blunted tip area, is that when using the "loss of resistance technique" the pressure loss can be sensed very soon after the tip penetrates into the epidural space.

The tip portion can have a blunted or rounded tip.

The plurality of holes 540 is in the superior face 524 and on an far distal portion of the inferior face 530 adjacent to the front edge 534. A bottom portion of the inferior face 530 can be covered by overlying sheath and may not have the holes.

The plurality of holes 540 can comprise between 5 and 10 holes in each face (inferior and superior face) and the holes can have a diameter between 0.5 and 1.5 mm and preferable about 1 mm.

Needle Shaft

The needle shaft can have an about rectangular or oval cross sectional shape. A second end of the needle shaft can have an attachment means for providing a fluid tight engagement with a fluid container. As shown in FIG. 6A, second end of the needle shaft can have a needle hub 582 for providing a fluid tight engagement with a fluid container (e.g., syringe).

Conduit Sheath

In an aspect needle can further comprises a conduit sheath 570. The needle 500 and conduit sheath 570 can be designed to be inserted together percutaneously (e.g., thru the skin) into an animal.

Referring to FIG. 6B, the conduit 570 has a channel 584 from a proximate end opening 580 to a distal opening 574 (needle tip opening). The sheath 570 in proximate to the distal opening 574 can have a tapered thin edge as shown in FIG. 5B.

The conduit sheath 570 and the needle 500 are adapted so that the needle fits in the channel and portions of the needle tip extend through the distal opening 574 to expose the superior face and portions of the inferior face (See FIG. 5B).

The opening in the conduit sheath can be skewed above the centerline to help direct a lead in the proper direction when inserted into the epidural space. See FIGS. 8A to 8B and description below.

Example Uses

The needle of this example embodiment can be used to insert tube for epidural anesthesia and to insert cylindrical percantaneous leads.

B. General Needle with Circular Cross Section and Symmetric Tip

Another example embodiment is a needle with holes in the tip section where the needle has at least a section about circular cross sections. This embodiment can be used to insert a cylindrical lead. This needle and sheath can be made smaller to the size to fit a cylindrical percutaneous lead.

FIGS. 7A thru 7E show views of an example embodiment needle.

FIG. 7A shows a bottom up view of the needle 700 shown in FIGS. 7B through 7E.

FIG. 7B shows a cross sectional view of the needle 700 shown in FIGS. 7A through 7E. FIG. 7B shows the inferior face 730 of the needle and the superior face 724. FIG. 7B shows sheath 770 extends upward to cover a portion of the bottom of the inferior needle face 730. Note that the tip 734 can be blunted. The tip 734 can be optionally on or off the midline or central axis of the needle.

FIG. 7C shows a top down view of the example embodiment's needle 700 showing the superior face 724, holes 740 in the tip section and sheath 770.

FIG. 7D shows a transverse cross sectional view through the tip section showing the sheath 770 over a portion of the inferior face of the needle 700 and the holes 740 in the tip section.

FIG. 7E shows a front end view of the tip section and a lower bottom face of the sheath 770 that overlies a lower (proximal) portion of the inferior face of the tip section of the needle 700.

The needle shaft can have a circular transverse cross section at least near the tip portion. The tip section has a superior face 724 and an inferior face 730. The area of the superior face can be about 50% of the area of the tip portion area and the area of the inferior face is about 50% of the area the tip portion.

Preferable, more than 50% of the holes 740 are in the superior face 724 and less than 50% of the holes 740 are in the inferior face.

The holes are preferable in the tip section, not in the junction between the tip section and shaft.

The needle shaft near the tip section can have a diameter between about 1 to 6 mm and the holes in tip section can have a diameter between about 0.3 to 0.6 mm and the needle tip section can have a circular cross sectional area.

The tip section can be in a blunt pencil shape.

Sheath

The sheath 770 can be adapted to have the needle 700 inserted into the sheath's lumen so that the needle tip section extends thru the sheath opening. When the needle and sheath are used to open a passage thru tissue to insert a lead, the sheath lumen should be large enough to allow the lead through.

Example Uses

The needle of this example embodiment can be used to insert sheath for epidural anesthesia and to insert round percantaneous leads. The example embodiments needle can have a round cross sectional area and can have a needle tip with a symmetric shape or an off-centered tip, but can have more holes (or hole area) on the superior side of the tip section.

An embodiment needle can have epidural use for anesthesia: cross section circular, multi hole, skewed tip, smaller size (about 17-20 gauge), with a sheath with skewed opening, for inserting epidural catheter (much smaller then the percutaneous lead) for epidural anesthesia.

An embodiment needle can have epidural use for percutaneous neurostimulation lead insertion: circular cross section, multi hole, skewed tip, larger size, (about 14-15 gauge), with sheath with skewed opening, for lead (much larger) insertion V. Example Embodiments for Methods Some example embodiments of the invention provide methods of placing a relative large foreign body, such as an electrical stimulation lead, in an animal with less invasive technique than the traditional means. For example, we can percutaneously access a site proximate to a desired lead placement site though formation of an access passage using a needle and overlying sheath. (e.g., sheath conduit, conduit). We can remove the needle while leaving the sheath in place. We can insert a lead thru the sheath and direct the lead further through an animal's tissue to the desired lead placement site. The needle, sheath and/or lead can be any capable needle, sheath and lead or can be any of the example embodiments' needle, sheath and/or lead used in any combination.

Figure 8A:
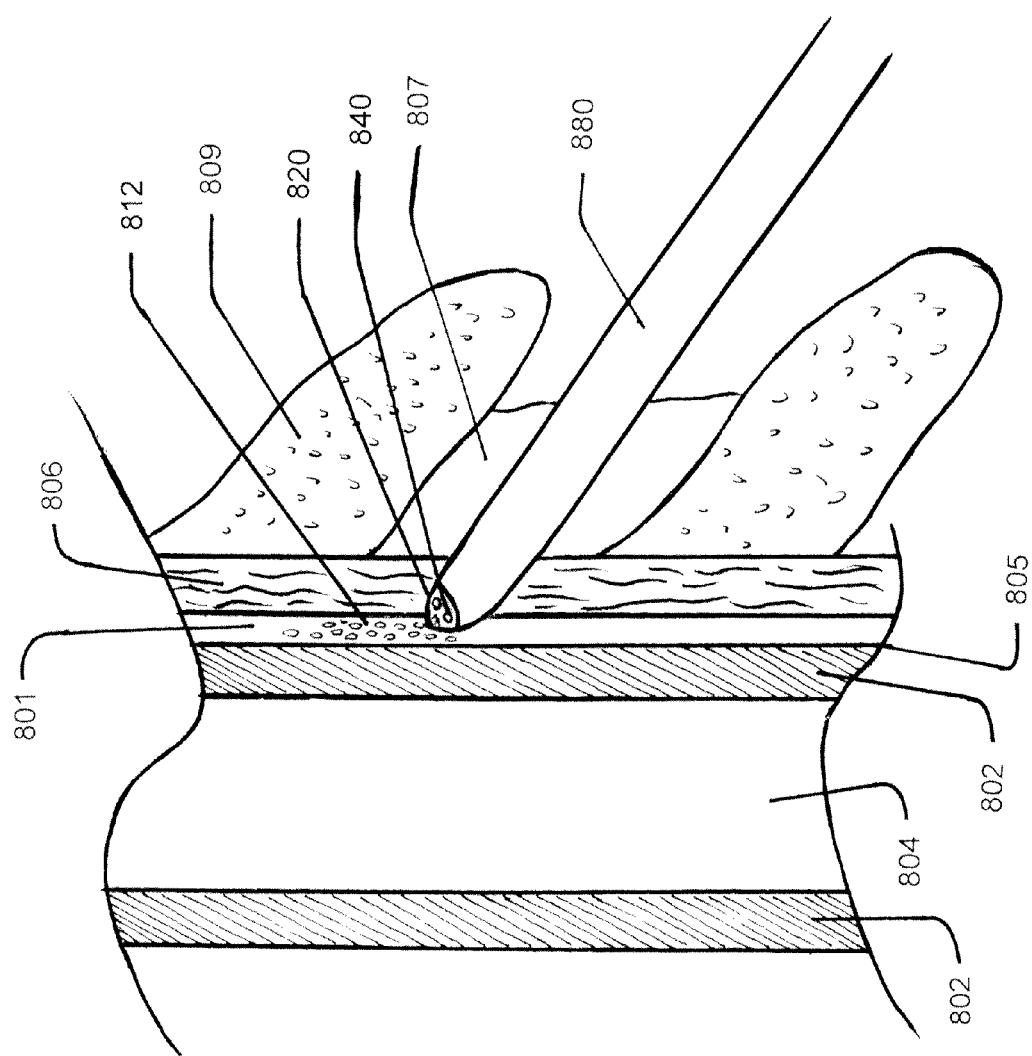

FIGS. 8A thru 8D show an example method for placing a lead in an epidermal space. FIG. 8A illustrates the tissues that define the epidural space 801 including the dura matter 805 (or dura) which separates subarachnoid space 802 from epidural space 801. The ligamentum flavum 806 which is a ligament adjacent to the dura 805 that runs longitudinally along the spinal column. Other anatomical structures shown in FIG. 8A near the epidural space 801 include the spinous process 809 and subarachnoid space 802 (filed with spinal fluid). To access the epidural space 801, the patient is positioned traditionally either seated or on their side and instructed to flex their back outward to maximize spacing between the outer vertebral components. The spinous processes are palpated, and the interlaminar space is estimated. If image technique such as fluoroscopy is used for needle guidance, patient is placed in prone or lateral position.

A needle trajectory is then chosen by the operator and a needle is inserted in the midline (midline approach) or on either side of the midline (peramedial approach). As the needle is advanced, it passes through (in order from the skin): soft tissue, interspinous ligament 807 (needle will bypass this structure if using paramedial approach), and ligamentum flavum 806 then ideally stops in the epidural space 801.

FIG. 8A illustrates placement of the needle and sheath 880 into the epidural space 801 using the "loss of resistance" technique. FIG. 8A is a sagittal cross sectional view of the epidural space 801 with adjacent structure, showing a properly placed needle, needle tip 820, holes 840 in needle tip, sheath 880 and a fluid 812 being injected into epidural space from a syringe that is rigidly connected to the needle.

Prior to encountering the ligamentum flavum 806, a specially designed glass or plastic low-resistance syringe (not shown, but see, e.g., FIG. 3C) filled with air or saline is attached to the needle. The needle then is advanced slowly and gentle pressure is maintained on the syringe plunger to constantly assess the resistance to flow/or resistance to attempted flow at the tip 820 of the needle. Further, the force to advance the needle can be gradually allocated more and more via pushing the syringe plunger as the needle tip is more and more engaged in a dense tissue as ligamentum flavum. This will render the process safer since at the moment a loss of resistance happens, the force to advance the needle will suddenly push the plunger in, leaving the syringe and more importantly, the needle at the same location.

A loss of resistance to flow, as assessed through subjective feel when the air or fluid 812 is ejected from the syringe, indicates that the needle tip 820 has passed through the ligamentum flavum 806 into the epidural space 801. The difference in the amount of resistance to injection results from the difference of tissue that forms the ligamentum flavum from the tissue that fills epidural space. The ligamentum flavum is composed of dense connective tissue, which is very resistant to expansion, while the epidural space is a potential space that is filled mostly with loose fatty tissue and venous plexus. Attempting to inject fluid or air into ligamentum flavum will meet large amount of resistance. When the epidural needle tip passes through ligamentum flavum 806 and enters into epidural space 801 the tip openings 840 are connected with epidural space 801, the operator typically will experience a feeling of sudden decrease of resistance to flow at the syringe plunger, indicating the needle tip 820 (at least the front portion) is within the epidural space 801.

By using the example embodiment's needle with multiple small holes in the tip section, loss of resistance is improved and is more sensitive since some of the holes are located purposefully at the far distal end of needle tip. The arrangement will allow a change in resistance at the very time the far distal end of the tip is entering the epidural space. Further, multiple small holes, as opposed to one large opening at needle tip will allow a significant increase in the size of the needle without jeopardizing epidural space access with loss of resistance technique. As the needle size increases, a single opening at needle tip will more and more likely to have a piece of tissue carved and stuck into the needle lumen, blocking the communication between the attached syringe and opening at the needle tip. This will render loss of resistance technique unusable. The holes (e.g., 540, 740) in the embodiments' needle tip can be sized to minimize the amount of tissue that plugs the holes during use.

FIG. 8B shows the needle withdrawn from the sheath 880. At least part of the conduit sheath opening is still in the ligamentium flavum 806.

FIG. 8C shows a flat probe 824, of similar size and shape to that of the lead but made of slightly more rigid material, that can be inserted through the sheath 880. This step is optional, and is for the purpose of cleaning up the passage. Based on the inventor's personal experience, the "Loss-of- Resistance" technique in this case will likely be very sensitive, meaning the opening to epidural space on ligamentium flavum will likely be small at the time "Loss-of-Resistance" is obtained and the epidural needle is withdrawn; and passage of the paddle lead may be difficult or not possible. To be sure an opening to epidural space is large enough, a flat shaped probe of similar size and shape to that of the paddle lead can be passed through the conduit before the insertion of the actual lead, after the epidural needle is withdrawn. This will likely initiate a blunt dissection if needed and extend the opening on ligamentium flavum. The probe should be made of flexible, soft material, such as silicon, but stiffer than the paddle lead, with a smooth, blunt and rounded end. This will allow the force for blunt dissection without cutting dura and piercing into subarachnoid space. Due to the large size of the probe and lead, the dura matter may be depressed during insertion by the probe and lead. In other words, the probe and lead may clear their own way while being inserted/advanced in the epidural space.

Figure 8D:
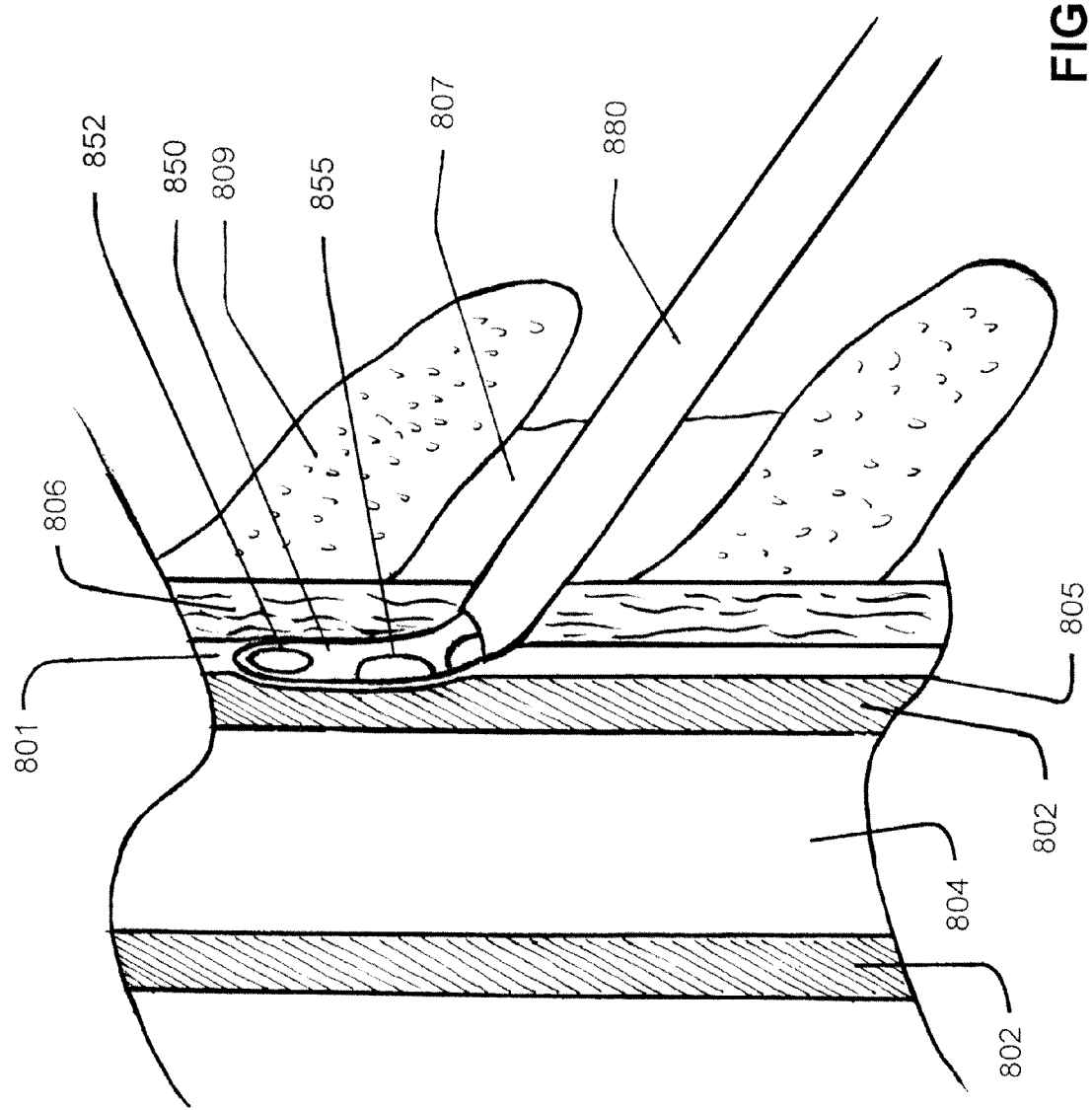

FIG. 8D shows a lead 850 inserted through the sheath 880 and directing the lead further through the epidural space 801 to the desired lead placement site. The sheath's off center opening is designed to direct the lead in the proper direction and position. The lead can have a tip marker 852 and electrodes 855. The lead can have the example embodiments' tip section that can change shape during insertion. The change in lead tip shape is controllable by the operator, and can be used to steer the lead into the proper position.

When using one of the example embodiment leads, the shape of the tip portion can be changeable during insertion into an animal whereby the lead can move in a desired direction.

When inserting a paddle style lead of an example embodiment, the tip portion is flexible and movable in a direction that is substantially parallel to a planar surface of the lead. This will change the length of one side of the tip section which will change the direction of the lead advancement within the epidural space.

Figure 8E:
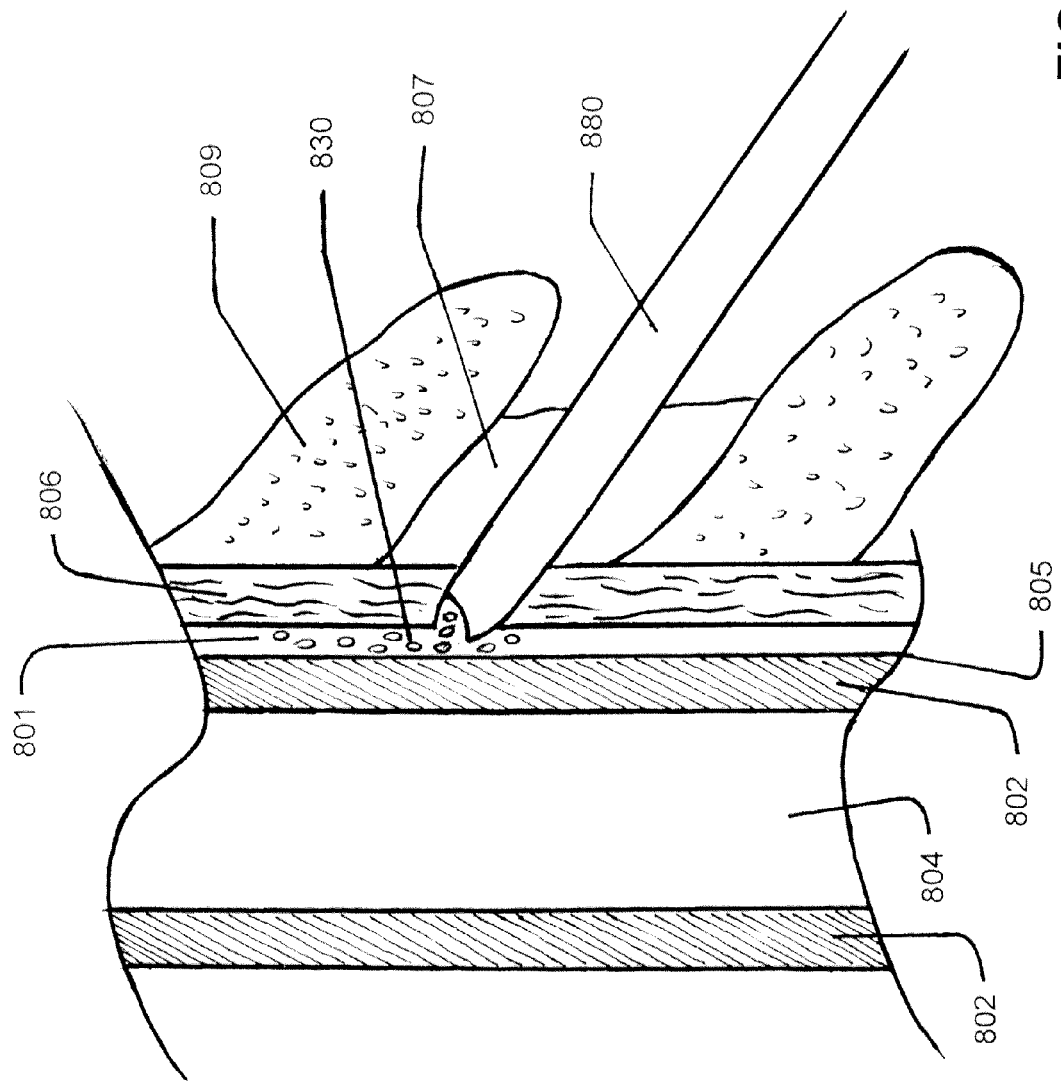
FIG. 8E shows the placement of a fluid or solid according to an example embodiment.

FIG. 8E shows another example embodiment where a solid or fluid 830 is introduced into the epidural space thru the sheath 880 lumen.

It is noted that the needles and/or sheaths of the example embodiments of the invention can be used with this method. Also, that example embodiment leads can also be used.

A. Non-Limiting Example Embodiments

The present invention provides a technique for positioning therapy delivery elements, such as electrodes or fluids or solids, optimally closer to the desired treatment area The present invention includes a therapy delivery device such as a signal generator, at least one lead having at least one therapy delivery element coupled to the therapy delivery device By using the foregoing techniques, therapy delivery elements may be positioned to provide treatment therapy such as electrical stimulation to a precise target.

Unless explicitly stated otherwise, each numerical value and range should be interpreted as being approximate as if the word about or approximately preceded the value of the value or range.

Given the variety of embodiments of the present invention just described, the above description and illustrations show not be taken as limiting the scope of the present invention defined by the claims.

While the invention has been particularly shown and described with reference to the preferred embodiments thereof, it will be understood by those skilled in the art that various changes in form and details may be made without departing from the spirit and scope of the invention. It is intended to cover various modifications and similar arrangements and procedures, and the scope of the appended claims therefore should be accorded the broadest interpretation so as to encompass all such modifications and similar arrangements and procedures.

What is claimed is:

1. A lead adapted to be steerable during insertion into an animal body, the lead comprising: a paddle-shaped structure having a proximate end and a distal end, the structure including a tip portion in the distal end, and a body portion proximal to the tip portion, the tip portion being configured to be manipulable relative to the body portion during insertion of the lead into an animal body such that the lead is moveable in a desired direction, and the tip portion having a first edge portion and a second edge portion; a manipulating structure at least partially within the tip portion configured to manipulate one of the first and second edge portions of the tip portion relative to the other of the first and second edge portions of the tip, the manipulating structure includes at least one expandable and contractible fluid chamber in at least said tip portion and at least one passage extending through at least the body portion and in fluid communication with the fluid chamber, wherein expansion or contraction of the fluid chamber manipulates the one of the first and second edge portions of the tip portion relative to the other of the first and second edge portions; and at least one electrode connected with the structure, the at least one electrode being positioned in the body portion.

2. The lead of claim 1 wherein an end of the tip portion defines an approximate V-shape.

3. A lead adapted to be steerable during insertion into a spinal column of an animal body, the lead comprising:
a paddle shaped structure having a proximate end, a central longitudinal axis, and a distal end, the structure including a tip portion formed in the distal end, and a body portion proximal to the tip portion, the tip portion being configured to be manipulable relative to the body portion, and having a first edge portion and a second edge portion;
at least two fluid chambers in the tip portion;
at least two passages extending through the body portion, each of the at least two passages being in fluid communication with a respective at least one of the two fluid chambers, each fluid chamber configured upon inflation or deflation to manipulate one of the first and second edge portions of the tip portion relative to the other of the first and second edge portions, whereby inflating or deflating at least one of the fluid chambers changes the shape of the tip portion only in a direction within a horizontal plane extending through the center of the lead and parallel to the central longitudinal axis; and
at least one electrode connected with the structure.

4. The lead of claim 1 wherein the manipulating structure includes at least one control wire passing through at least one channel extending from the body portion to the tip portion.

5. A lead adapted to be steerable during insertion into an animal body, the lead comprising: a paddle-shaped structure having a proximate end, and a distal end, the structure including a tip portion in the distal end, and a body portion proximal to the tip portion, the tip portion being configured to be manipulable relative to the body portion during insertion into an animal body such that the lead is moveable in a desired direction, the tip portion having a first edge portion and a second edge portion; at least one fluid chamber in at least the tip portion, and at least one passage extending through the body portion, and the passage being in fluid communication with the at least one fluid chamber wherein the volume of fluid within the at least one chamber can be changed to inflate or deflate the at least one fluid chamber, the at least one fluid chamber is configured upon inflation or deflation for controlled manipulation of one of the first and second edge portions relative to the other of the first and second edge portions; and at least one electrode connected with the structure, the at least one electrode being positioned in the body portion.

6. The lead of claim 5 wherein the tip portion defines an approximate V-shape terminating in a blunted tip.

7. The lead of claim 5 wherein the body portion includes (a) a plurality of electrodes, and (b) a conductor of a plurality of conductors electrically coupling at least one terminal of a plurality of terminals with at least one electrode of the plurality of electrodes.

8. The lead of claim 5 wherein the at least one passage extends from the proximate end of the body portion to the tip portion; and
   at least one tube in fluid communication with said at least one passage.

9. The lead of claim 5 which further comprises a device for introducing, or withdrawing, fluid from the at least one fluid chamber through at least one respective passage, the device being in fluid communication with the at least one respective passage, and the tip portion defining a plurality of folds to assist in manipulation of the tip portion.

10. The lead of claim 5 which further includes a tip marker proximate the distal end, the tip marker being observable in the animal body using an imaging technique.

11. A combination comprising:
   a. the lead of claim 1;
   b. a needle; and
   c. a sheath having a channel adapted to receive at least a portion of the needle therein, wherein the lead is adapted to be inserted into the animal body through the sheath after placement of the sheath in the animal body using the needle.

12. The lead of claim 1 wherein the manipulating structure includes a stylet passing through a channel in said lead structure extending from portions of the body to the tip portion, a distal end of the stylet removably extends into the tip portion during insertion.

13. The lead of claim 1 which further comprises a stylet passing through a channel along the midline of the lead structure extending from portions of the body portion to the tip portion, the stylet having a bent or curved section within the tip portion wherein rotating the stylet manipulates the one of the first and second edge portions of the tip portion relative to the other of the first and second edge portions of the tip portion, wherein the paddle-shaped structure includes the body portion and the tip portion.

* * * * *